(12) United States Patent
Iwasaki et al.

(10) Patent No.: US 7,646,849 B2
(45) Date of Patent: Jan. 12, 2010

(54) ULTRA-SMALL ANGLE X-RAY SCATTERING MEASURING APPARATUS

(75) Inventors: Yoshio Iwasaki, Tokyo (JP); Yutaka Yokozawa, Tokyo (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 127 days.

(21) Appl. No.: 11/774,138

(22) Filed: Jul. 6, 2007

(65) Prior Publication Data
US 2008/0013685 A1  Jan. 17, 2008

(30) Foreign Application Priority Data
Jul. 7, 2006  (JP) .............................. 2006-187828

(51) Int. Cl.
*G01N 23/201* (2006.01)
*G01N 23/20* (2006.01)
(52) U.S. Cl. .......................................... 378/86; 378/70
(58) Field of Classification Search .............. 378/70–90
See application file for complete search history.

(56) References Cited

U.S. PATENT DOCUMENTS

| | | | | |
|---|---|---|---|---|
| 5,016,267 | A * | 5/1991 | Wilkins ........................ | 378/84 |
| 5,115,460 | A * | 5/1992 | De Lange .................... | 378/150 |
| 5,199,058 | A * | 3/1993 | Tani et al. ..................... | 378/82 |
| 5,485,499 | A * | 1/1996 | Pew et al. ..................... | 378/84 |
| 6,529,578 | B1 | 3/2003 | Taguchi et al. | |
| 6,704,390 | B2 * | 3/2004 | Kogan .......................... | 378/84 |
| 2002/0003857 | A1 * | 1/2002 | Koyanagi ...................... | 378/70 |
| 2002/0080916 | A1 * | 6/2002 | Jiang et al. .................... | 378/84 |
| 2003/0123610 | A1 * | 7/2003 | Okanda et al. ................ | 378/71 |

(Continued)

FOREIGN PATENT DOCUMENTS

FR  2 850 171  7/2004

(Continued)

OTHER PUBLICATIONS

Gehrke et al., "Ultrasmall-Angle X-Ray Scattering at the HASYLAB Wiggler Beamline BW4" Rev. Sci. Instrum., 1995, vol. 66, No. 2, pp. 1354-1356.

(Continued)

*Primary Examiner*—Edward J Glick
*Assistant Examiner*—Anastasia Midkiff
(74) *Attorney, Agent, or Firm*—Buchanan Ingersoll & Rooney PC

(57) ABSTRACT

An ultra-small angle X-ray scattering measuring apparatus includes a detector for detecting X-rays emitted from a sample, an X-ray collimating mirror arranged between the X-ray real focus and the sample, a monochromator arranged between the X-ray collimating mirror and the sample and an analyzer arranged between the sample and the detector. The X-ray collimating mirror includes a pair of X-ray mirrors that are arranged orthogonally relative to each other. The X-ray mirrors are multilayer film mirrors and their X-ray reflection surfaces are paraboloidal. The interplanar spacing of lattice planes of each of the multilayer films is continuously changed along the paraboloid so as to meet the Bragg's condition. The monochromator and the analyzer are formed by using a channel-cut crystal. The analyzer is driven to rotate for scanning around a $2\theta$-axial line and diffracted rays reduced to a spectrum by the analyzer are detected by the detector.

10 Claims, 13 Drawing Sheets

U.S. PATENT DOCUMENTS

| | | | |
|---|---|---|---|
| 2004/0096034 A1* | 5/2004 | Michaelsen et al. | 378/70 |
| 2004/0190681 A1* | 9/2004 | Omote | 378/71 |
| 2006/0018429 A1* | 1/2006 | Hoghoj et al. | 378/84 |
| 2006/0176998 A1* | 8/2006 | Korsunsky | 378/71 |
| 2007/0007464 A1* | 1/2007 | Lange et al. | 250/390.1 |

FOREIGN PATENT DOCUMENTS

| | | |
|---|---|---|
| JP | 2001-356197 A | 12/2001 |
| JP | 2005530168 | 10/2005 |
| WO | WO 99/43009 | 8/1999 |

OTHER PUBLICATIONS

Ise et al., "X-Ray Scattering Study of Ionic Colloidal Crystals" Current Opinion in Colloid & Interface Science, 2001, vol. 6, pp. 126-131.

European Search Report dated Sep. 27, 2007.

Bonse et al, "Small Angle X-Ray Scattering by Spherical Particles of Polystyrene and Polyvinyltoluene", Zeitschrift fuer Physik 189, pp. 151-162 (1966).

Koga et al, "Development of a High Flux and High Temperature Set-Up Bonse-Hart Ultra-Small-Angle X-ray Scattering (USAXS) Diffractometer", Meeting abstracts of the Physical Society of Japan, vol. 51, No. 2, Mar. 15,1996, p. 580.

Konishi et al, "Single Crystal of colloidal silica particles in a dilute aqueous dispersion as studied by two-dimensional ultrasmall-angle x-ray scattering", Physical Review B, vol. 57, Issue 5, Feb. 1, 1998, pp. 2655-2658.

M. Birkholz, "Thin Film Analysis by X-Ray Scattering," Wiley-Vch Verlag GmbH & Co. KGaA, pp. 31-35, 2006.

* cited by examiner

<STANDARD STEREO PROJECTION OF
(001) PLANE IN CUBIC CRYSTAL SYSTEM>

ULTRA-SMALL ANGLE X-RAY SCATTERING MEASURING APPARATUS

BACKGROUND OF THE INVENTION

1. Field of the Invention

This invention relates to an X-ray small angle scattering measuring apparatus for measuring scattered rays emitted from a sample in a small angle region. In particular, the present invention relates to an ultra-small angle X-ray scattering measuring apparatus that can suitably be employed to measure scattered rays within such an ultra-small angle region that the angle of $2\theta$-diffraction is defined as $2\theta \leq 0.08°$.

2. Description of the Related Art

The X-ray small angle scattering method is known as a technique of determining the sizes and the shapes of crystal particles in the inside of a substance by observing X-ray scattering in a small angle region of $2\theta$-diffraction angle, e.g. $0° \leq 2\theta \leq 5°$. Slit type X-ray small angle scattering measuring apparatuses have been known as apparatuses which realize the X-ray small angle scattering method. Some kinds of slit type X-ray small angle scattering measuring apparatuses have been known, such as an X-ray small angle scattering measuring apparatuses employing an optical system that has three slits and an X-ray small angle scattering measuring apparatuses employing a Kratky U-slit.

Japanese Patent Laid-Open Publication No. 2001-356197 discloses an exemplar 3-slit type X-ray small angle scattering measuring apparatus. The disclosed X-ray small angle scattering measuring apparatus is adapted to limit divergence (or spreading) of X-rays entering a sample by means of the first and second slits to form parallel X-rays and obtain scattered rays in a small angle region from a sample by irradiating the sample with the parallel X-rays. The third slit exerts the effect of eliminating scattered rays emanated from the first and second slits. An X-ray small angle scattering measuring apparatus that employs the Kratky U-slit can realize a resolution higher than the 3-slit type X-ray small angle scattering measuring apparatus by controlling divergence of X-rays by means of the Kratky U-slit that is a block-shaped member.

Meanwhile, there has been an increasing demand, or desire, for clearly capturing scattered rays in an ultra-small angle region ($2\theta \leq 0.08°$) in order to analyze the aggregate structure of a higher order of molecules of a polymer material such as plastic and rubber. In principle, it may be possible to analyze such an aggregate structure to meet the demand by measuring X-ray small angle scattering by means of a 3-slit type X-ray small angle scattering measuring apparatus or an X-ray small angle scattering measuring apparatus employing the Kratky U-slit. In reality, however, it is not possible to meet the demand for analyzing such an aggregate structure by means of an X-ray small angle scattering measuring apparatus of either type. The reason is that it is difficult for both the 3-slit type and the Kratky U-slit type X-ray small angle scattering measuring apparatuses to narrow the divergence angle of X-rays entering a sample, while maintaining the intensity of the X-rays to a high level, so that it is not possible to clearly remove the background in an ultra-small angle region and hence capture scattered rays from the sample in the ultra-small angle region.

X-ray small angle scattering measuring apparatuses employing a Bonse-Hart optical system have been known as X-ray small angle scattering measuring apparatuses designed to obtain information on scattered rays in an ultra-small angle region. As shown in FIG. 12A of the accompanying drawings as an example, such a device has a structure in which a monochromator 101 formed by using a channel-cut crystal is arranged between a sample S and an X-ray source 102 and an analyzer 103 also formed by using a channel-cut crystal is arranged between the sample S and an X-ray detector 104.

In FIG. 12A, reference symbols X, Y and Z indicate three-dimensional directions. The Z-direction is the direction perpendicular to the plane of FIG. 12A. In a measuring operation, as the analyzer 103 is driven to rotate for scanning around the axial line $X_0$ of the analyzer 103 itself (so-called $2\theta$-rotation), it is possible to observe the change in the intensity I of scattered rays that corresponds to the change of $2\theta$-angle as shown in FIG. 12B. The $2\theta$-direction is the direction of rotation around the axial line $X_0$ that is perpendicular to the XY plane. The XY plane is a plane that includes the optical axis $X_1$ of X-rays extending from the X-ray source 102 to the X-ray detector 104 and orthogonal relative to the axial line $X_0$ of $2\theta$-rotation. The XY plane may also be referred to as equatorial plane. The direction perpendicular to the equatorial plane that extends in the Z-direction may be referred to as latitudinal direction.

In an ultra-small angle X-ray scattering measuring apparatus employing a Bonse-Hart optical system, a parallel X-ray beam is formed not by partly removing X-rays emitted from the X-ray source 102 by means of a slit or slits, but by causing X-rays to be diffracted (namely be reflected) by the channel-cut crystal 101. At this time, the channel-cut crystal 101 also performs monochromatization that converts an X-ray beam containing X-rays of different wavelengths to a monochromatic (e.g. $K\alpha1$) X-ray beam. Therefore, the aforesaid ultra-small angle X-ray scattering measuring apparatus may irradiate a sample with a parallel and monochromatic X-ray beam. Further, with use of the analyzer 103, the precise monochromatic X-ray beam is directed to the X-ray detector 104. Thus, the ultra-small angle X-ray scattering measuring apparatus employing a Bonse-Hart optical system has been said to be capable of measuring scattered rays generated by the sample S in an ultra-small angle region.

However, the inventor of the present invention conducted an experiment and found that it was not possible to accurately capture scattered rays from a sample in an ultra-small angle region even by using a Bonse-Hart optical system. The reason for this is that divergence (namely spreading) of X-rays can not be limited in the latitudinal direction that is perpendicular to the equatorial plane, while the resolution in intra-equatorial-plane directions can be maintained high, e.g., to about $0.002°$ because divergence (or spreading) of X-rays can be limited in the equatorial plane by means of a monochromator and an analyzer. Note that the equatorial plane means the plane in which the X-ray detector is driven to move for scanning in order to capture scattered rays from a sample, and further means the plane in which the analyzer crystal 103 is driven to rotate in $2\theta$-rotation. When divergence (spreading) of X-rays is not limited in the latitudinal direction, a smearing phenomenon arises resulting in failing to accurately capture the pattern of scattered rays emitted from a sample.

A smearing phenomenon may also be referred to as a blurring/staining phenomenon that can arise when a plurality of Debye rings that are formed due to scattered rays from a sample are found one on the other in the X-ray detection region of the X-ray detector and stains the Debye rings that have been actually captured and makes them unclear. Now, a smearing phenomenon will be described in greater detail below by referring to FIGS. 13A and 13B of the accompanying drawings.

A smearing phenomenon appears when the width of X-rays entering a sample is sufficiently broader than the Debye rings of scattered rays arising from the sample. FIG. 13A schematically illustrates how incident X-rays $R_0$ enter the sample S to produce scattered rays $R_1$. Scattered rays $R_1$ include a plurality of Debye rings D that are found one on the other. The width $W_0$ of the incident X-rays $R_0$ is sufficiently broader than the Debye rings forming scattered rays $R_1$.

In FIG. 13A reference symbols X, Y and Z depict a three-dimensional space. The X-ray detector is driven to rotate in a manner of a 2θ-rotation around the Z-axis to detect scattered rays $R_1$. In other words, the XY plane is an equatorial plane and the Z-direction that is perpendicular to the XY plane is the latitudinal direction. FIG. 13A illustrates a phenomenon observed in an ultra-small angle region (e.g., 2θ≦0.08°). The width $W_0$ is so small that it may be contained in the X-ray optical axis of a wide-angle diffractometer, which may be a powder X-ray diffractometer.

From the viewpoint of ideal observation, the detection region $A_0$ of a zero-dimensional X-ray detector such as an SC (scintillation counter) is supposed to detect a single Debye ring. If such is the case, a scattering pattern (Gaussian distribution pattern) A that is attributable to a single Debye ring is detected in FIG. 13B. However, when scattered rays $R_1$ include a plurality of Debye rings D that are found one on the other, the detection region $A_0$ detects those large number of Debye rings so that a scattering pattern B as indicted by symbol B in FIG. 13B that is attributable to a plurality of Debye rings is detected. In other words, when a smearing phenomenon occurs, significant peak information that indicates the sizes and the shapes of crystal particles that are present in a sample is buried in the background that arises due to a large number of Debye rings produced according to a broad X-ray beam width and hence cannot be detected.

With a Bonse-Hart optical system as shown in FIG. 12A, divergence (spreading) of X-rays in intra-equatorial-plane directions (namely intra-XY-plane directions) may be controlled by means of monochromator crystals. Therefore, it may be safe to assume that the influence of a smearing phenomenon in intra-equatorial-plane directions does not adversely affect the results of observation. However, since divergence (spreading) of X-rays is not controlled in the latitudinal direction (Z-direction), the sample S is irradiated with X-rays having broad width in the latitudinal direction to probably give rise to a smearing phenomenon. Then, it may not be possible to accurately capture the pattern of scattered rays in an ultra-small angle region due to the smearing phenomenon.

In FIG. 12A, a technique of narrowing the X-ray beam width in the latitudinal direction (Z-direction) by means of a slit or slits may be conceivable, for the purpose of dissolving the smearing phenomenon in the latitudinal direction. It may appear that Debye rings overlapping with each other within an ultra-small angle region (2θ≦0.08°) are reduced in number by means of such a technique so that the pattern of scattered rays may be accurately captured. However, the intensity of X-rays is made too weak to make it no longer possible to accurately observe X-rays when a slit is employed to control the width of an X-ray beam.

SUMMARY OF THE INVENTION

In view of the above-identified problems, it is therefore an object of the present invention to provide an ultra-small angle X-ray scattering measuring apparatus that can accurately capture the pattern of scattered rays emitted from a sample in an ultra-small angle region by suppressing the smearing phenomenon.

In the first aspect of the present invention, the above object is achieved by providing an ultra-small angle X-ray scattering measuring apparatus comprising: an X-ray generation device for taking out X-rays radiated from an X-ray real focus with a predetermined focus size and emitting them toward a sample; an X-ray detection device for detecting X-rays emitted from the sample; an X-ray collimating mirror arranged between the X-ray real focus and the sample; a monochromator arranged between the X-ray collimating mirror and the sample; and an analyzer arranged between the sample and the X-ray detection device. The X-ray collimating mirror includes a first mirror and a second mirror that are orthogonal relative to each other. The first mirror and the second mirror have a multilayer film formed by alternately laying layers of a heavy element and those of a light element so as to operate as X-ray reflection surface, which multilayer film shows a profile of a paraboloid. The interplanar spacing of lattice planes of the multilayer film is made to continuously change along the paraboloid so as to satisfy the Bragg's condition for diffraction at any arbitrarily selected position on the X-ray reflection surface relative to X-rays of a specific wavelength. The monochromator and the analyzer have a pair of oppositely disposed X-ray reflection surfaces and are formed by using a perfect crystal. The analyzer is driven to rotate for scanning around a 2θ-axial line that is orthogonal relative to the X-ray optical axis running through the analyzer and X-rays are detected by the X-ray detector at every angular position within the rotation for scanning.

With the above-described arrangement, the expression that the X-ray generation device takes out X-rays with a predetermined focus size refers to that it typically takes out point-focused X-rays or line-focused X-rays. Point-focused X-rays refer to X-rays showing a cross section that is a circle, square or polygon close to a circle. Line-focused X-rays refer to X-rays showing a cross section that is rectangle or a polygon close to a rectangle.

The size of the X-ray focus is often 0.5 mm×1 mm (meaning effective focus size when viewed from an oblique viewing angle of 6°) in known slit type X-ray small angle scattering measuring apparatus and X-ray small angle scattering measuring apparatus employing a Bonse-Hart type optical system. Of course, it is possible to use such a conventional focus size in the present invention. However, a smaller focus size may be applicable to the measuring apparatus according to the present invention because an X-ray collimating mirror that is a multilayer film paraboloid mirror is arranged between the X-ray source and the monochromator. According to the inventor's experiments, it was possible to adopt a focus size not smaller than 0.05 mm in diameter and not greater than 0.1 mm in diameter, preferably 0.08 mm in diameter (respectively meaning effective focus size when viewed from an oblique viewing angle of 6°). When the focus size is made small, it is possible to reduce the width of the parallel X-ray beam entering a sample, and such a size reduction is desirable from the viewpoint of preventing a smearing phenomenon from taking place. Note that the expressions of 0.05 mm in diameter, 0.08 mm in diameter and 0.1 mm in diameter do not only refer to the diameters of perfect circles but also refer to the effective focus sizes of rounded squares of 0.05 mm×0.05 mm, 0.08 mm×0.08 mm and 0.1 mm×0.1 mm.

When the focus size is reduced, it is possible to reduce the power supply capacity and hence it is desirable to reduce the focus size from this point of view. Note that although an 18 kW rotating anti-cathode type X-ray source has been employed for the conventional focus size of 0.5 mm×1 mm, a 0.8 kW or 1.2 kW rotating anti-cathode type X-ray source may be employed for a focus size being not smaller than 0.05 mm (50 μm) in diameter and not greater than 0.1 mm (100 μm) in diameter, preferably 0.08 mm (80 μm) in diameter.

In an ultra-small angle X-ray scattering measuring apparatus according to the present invention and having the above-described configuration, an X-ray collimating mirror formed by arranging a first mirror and a second mirror orthogonally relative to each other and is arranged in front of a monochromator and the X-ray reflection surface of the first mirror and that of the second mirror are paraboloidal. Therefore, X-rays emitted from an X-ray source are two-dimensionally collimated, in other words collimated in both the longitudinal direction and the transversal direction. Thus, the cross section of the collimated X-ray beam shows a rectangular or rhombic contour.

Additionally, the X-ray reflection surface of the X-ray collimating mirror is formed by alternately laying layers of a heavy element and those of a light element. Still additionally, the interplanar spacing of lattice planes of the multilayer film is made to continuously change along the paraboloid so as to satisfy the Bragg's condition for diffraction at any arbitrarily selected position on the X-ray reflection surface relative to X-rays of a specific wavelength. Thus, all the X-rays that enters the X-ray collimating mirror are transformed into a monochromatic and parallel X-ray beam whose intensity is very strong. The intensity is by far stronger than that of a parallel X-ray beam obtained by narrowing the diameter of the beam by means of one or more than one slits. The intensity is satisfactorily strong for generating sufficiently strong scattered rays for the purpose of observations from a sample in an ultra-small angle region (namely $2\theta \leq 0.08°$).

As described above, according to the present invention, it is possible to irradiate a sample with two-dimensionally collimated highly intense monochromatic X-rays. Thus, any smearing phenomenon that is observed when X-rays are collimated only in a one-dimensional direction as in the case of conventional Bonse-Hart optical systems is prevented from taking place, so that it is possible to clearly capture the pattern of scattered rays from a sample in an ultra-small angle region (namely $2\theta \leq 0.08°$). Therefore, it is now possible to observe the electron density of a cluster of a structure of 200 nm to 1 µm (the cluster meaning an aggregate of atoms and molecules) by way of ultra-small X-ray scattering that is scarcely accompanied by a smearing phenomenon in order to find functional features of substances.

Furthermore, when X-rays are irradiated onto a cubic crystal system having a structure as illustrated by a stereo projection chart in FIG. 9A with a lattice constant of 400 nm, four spots are observed from the four lattice planes of (−100), (010), (100) and (0−10). Additionally, as shown in FIG. 9B, diffracted rays appear in two directions including the equatorial direction (or the out-of-plane direction) and the latitudinal direction (or the in-plane direction). Diffracted rays in the equatorial direction are those from (010) plane, whereas diffracted rays in the latitudinal direction are those from (−100) plane. In the case of a conventional Bonse-Hart optical system adapted to collimate X-rays only in the equatorial direction, a smearing phenomenon takes place in the latitudinal direction to increase the background, or noises so that it is not possible to observe diffracted rays in the latitudinal direction.

To the contrary, with an ultra-small angle X-ray scattering measuring apparatus according to the present invention, it is possible to collimate X-rays also in the longitudinal direction by controlling the divergence angle (namely spreading angle) to less than a predetermined value (e.g., not greater than 0.06°) in the longitudinal direction by means of the operation of the X-ray collimating mirror. Then, as a result, it is possible to suppress appearances of a smearing phenomenon in the longitudinal direction. In addition to the effect of suppressing appearances of a smearing phenomenon, the intensity of X-rays is enhanced due to the effect of the multilayer film in the measuring apparatus according to the present invention. Therefore, the present invention provides an advantage of being capable of simultaneously observing diffracted rays both in the equatorial direction and in the latitudinal direction shown in FIG. 9B.

In general, it is possible to change the diffraction angle by which X-rays diffract on the sample in both intra-equatorial-plane directions and in the latitudinal direction, by driving the sample for intra-planar rotation to thereby rotate the cubic crystal system in the direction of arrow φ in FIG. 9A. The measuring apparatus according to the present invention can clearly detect such a change of the diffraction angle. Then, if we observe the change in the diffraction angle of X-rays in response to the change of the intra-planar angle φ, we may find out accurately the crystallinity of the sample including a plurality of cubic crystal systems or other kind of crystal systems. The crystallinity means, for example, the orientation of lattice planes and the uniformity of the interplanar spacing of lattice planes.

Preferably, in an ultra-small angle X-ray scattering measuring apparatus according to the present invention, the X-ray detection device is a zero-dimensional X-ray detector that has an aperture for taking in X-rays and outputs a signal of the intensity of X-rays without spatial resolution on the X-rays taken in through the aperture. In an ultra-small angle X-ray scattering measuring apparatus according to the present invention, scattered ray data are obtained from the sample when the analyzer being driven for 2θ-rotation and the X-ray detection device being arranged in a positionally unmovable state. Therefore, the X-ray detection device is preferably a detector that can transform the X-rays taken in through the X-ray aperture into a signal without giving spatial resolution. The X-ray detection device may be a zero-dimensional X-ray detector such as an SC (scintillation counter) or a PC (proportional counter). Alternatively, it is also possible to use a one-dimensional X-ray detector having a position resolving power in a linear direction such as a PSPC (position sensitive proportional counter).

The relationship between the effective focus size of the X-ray source and the distance between the X-ray source and the center of the X-ray collimating mirror is preferably determined on the basis of the full width at half maximum intensity (or FWHM) of the rocking curve of the X-ray collimating mirror itself. The full width at half maximum intensity (or FWHM) of the rocking curve indicates the divergence (or spreading) angle of the X-ray beam. In other words, if the effective focus size of X-rays is "$F_p$", the FWHM of the rocking curve is "w" and the distance between the X-ray source and the center of the X-ray collimating mirror is "L", it is preferable that their relationship expressed by the following equation holds true.

$$F_p = \tan(w) \times L \qquad (1)$$

For example, if the FWHM of the rocking curve is 0.04°, the effective focus size of X-rays ($F_p$) is optimally 0.087 mm in diameter when the distance between the X-ray source and the center of the X-ray collimating mirror is 125 mm. The optimal value of the distance L between the X-ray source and the center of the mirror is approximately 71 mm when $F_p$ is 0.05 mm in diameter. Likewise, the optimal value of the distance L between the X-ray source and the center of the mirror is approximately 143 mm when $F_p$ is 0.1 mm in diameter. According to the inventor's consideration, it is found that the distance L between the X-ray source and the center of the mirror is desirably 70 mm≦L≦145 mm corresponding to the X-ray focus size of a diameter not smaller than 0.05 mm and not greater than 0.1 mm.

Generally, it is possible to raise the intensity of X-rays emitted from a target as a whole by employing a large effective focus size for the X-ray source. However, in the arrangement according to the present invention where an X-ray collimating mirror is placed at the back of X-ray source, even if the effective focus size is only simply increased for the X-ray source, X-rays that can be received by the X-ray collimating mirror is limited in quantity. In short, it is meaningless to unnecessarily increase the effective focus size for the X-ray source. On the other hand, it is advantageously possible to raise the luminance of the X-ray focus and receive all the X-rays emitted from the X-ray real focus by the X-ray collimating mirror by reducing the effective focus size for the X-ray source. However, the target can be molten and damaged when the effective focus size is made too small for the X-ray source. In other words, there is a limit for reducing the effective focus size for the X-ray source. Thus, determining the effective focus size $F_p$ of X-rays by the above formula (1) is highly advantageous for receiving X-rays generated by the X-ray source in an optimal condition and acquiring collimated X-rays showing an intensity that is as high as possible from the X-ray collimating mirror.

When arranging an X-ray generation device and an X-ray collimating mirror in a manner as described above, we may take full advantage of X-rays emitted from the X-ray source. Because of this advantage, we may use an X-ray generator having a lowly rated output power thereby to reduce the cost of the X-ray generator itself and also the cost of electric power and cooling water being respectively used for the operation of the X-ray generator.

Preferably, in an ultra-small angle X-ray scattering measuring apparatus according to the present invention, the heavy element and the light element for forming the multilayer film of the X-ray collimating mirror are respectively Ni (nickel) and carbon. However, for the purpose of the present invention, the heavy element and the light element are not limited to those. For example, W (tungsten) or Pt (platinum) may alternatively be used for the heavy element whereas Si (silicon) may alternatively be used for the light element. More specifically, the use of an X-ray collimating mirror formed by using a combination of Ni and carbon provided the best results in an experiment conducted by the inventor of the present invention.

Preferably, an ultra-small angle X-ray scattering measuring apparatus according to the present invention has a four-quadrant slit for controlling the vertical and transversal widths of X-rays entering the monochromator, a four-quadrant slit for controlling the vertical and transversal widths of X-rays emitted from the monochromator and an X-ray absorption member for attenuating the intensity of the direct beam. The four-quadrant slit arranged in front of the monochromator (and hence at the side of the X-ray collimating mirror) provides an effect of cutting out the first time reflection and other unnecessary reflections produced at the X-ray collimating mirror and taking in only the second time reflection that is necessary. Meanwhile, the four-quadrant slit provided between the monochromator and the sample provides an effect of cutting out Kα2 rays.

The ultra-small angle region (2θ≦0.08°) is the region where the direct beam proceeds. Generally, the ultra-small angle is measured with the direct beam in order to accurately know the angle 2θ=0° (meaning the position of the direct beam). To measure intense scattered rays being present near the direct beam, it is necessary to attenuate the intensity of the direct beam by arranging an X-ray absorption member on the optical axis of X-rays. Such an X-ray absorption member may be referred to as attenuator or an absorber. The X-ray absorption member is formed of a substance that can suppress penetration of X-rays, which may typically be Al (aluminum). In actuality, it is desirable to prepare Al members having (e.g., four) different thicknesses and selectively use an Al member that shows an appropriate X-ray attenuation ratio depending on the type of observation.

In the second aspect of the present invention, there is provided an ultra-small angle X-ray scattering measuring apparatus comprising an X-ray generation device for taking out X-rays radiated from an X-ray real focus with a predetermined focus size and emitting them toward a sample, an X-ray detection device for detecting X-rays emitted from the sample, an X-ray collimating mirror arranged between the X-ray real focus and the sample, a monochromator arranged between the X-ray collimating mirror and the sample, and an analyzer arranged between the sample and the X-ray detection device. The analyzer is driven to rotate for scanning around a 2θ-axial line in order to detect scattered rays from the sample. The 2θ-axial line is orthogonal relative to the X-ray optical axis extending from the X-ray real focus to the X-ray detection device. The X-ray collimating mirror is a composite X-ray mirror having two paraboloidal multilayer film X-ray reflection surfaces so as to make X-rays emitted from the X-ray generation device have a rhombic cross section. Each of the monochromator and the analyzer is a channel-cut crystal for controlling divergence (or spreading) of X-rays in the intra-equatorial-plane containing the X-ray optical axis and perpendicular to the 2θ-axial line. The X-ray detection device is adapted to detect X-rays emitted from the analyzer.

In an ultra-small angle X-ray scattering measuring apparatus according to the second aspect of the present invention, an X-ray collimating mirror is arranged in front of the monochromator so as to collimate X-rays emitted from the X-ray real focus that is an X-ray source so as to make the beam of X-rays have a rhombic cross section, or two-dimensionally collimated X-rays in the longitudinal direction and in the transversal direction. Additionally, since the X-ray reflection surface of the X-ray collimating mirror is a paraboloidal multilayer film, all the X-rays that enter the X-ray collimating mirror are transformed into a monochromatic and parallel X-ray beam whose intensity is hence very strong. The intensity is by far stronger than the intensity of X-rays that is obtained when the diameter of the parallel beam is narrowed by means of one or more than one slits, and hence sufficient with regard to generating scattered rays with a sufficient intensity in an ultra-small angle region (2θ≦0.08°) for the purpose of observation.

As described above, according to the present invention, it is possible to irradiate a sample with two-dimensionally collimated highly intense monochromatic X-rays. Thus, any smearing phenomenon that is observed when X-rays are collimated only in a one-dimensional direction as in the case of conventional Bonse-Hart optical systems is prevented from taking place, so that it is possible to clearly capture the pattern of scattered rays from a sample in an ultra-small angle region (namely 2θ≦0.08°). Therefore, it is now possible to observe the electron density of a cluster of a structure of 200 nm to 1 μm (the cluster meaning an aggregate of atoms and molecules) by way of ultra-small X-ray scattering that is scarcely accompanied by a smearing phenomenon in order to find functional features of substances.

An ultra-small angle X-ray scattering measuring apparatus according to the invention may additionally comprise a sample support device for supporting a sample. Preferably, the sample support device has a φ-rotary system for driving a sample to rotate in an intra-plane around a φ-axial line that intersects the X-ray receiving surface of the sample in order to detect data by changing the angles of the lattice planes relative to incident X-rays.

It is difficult for conventional ultra-small angle X-ray scattering measuring apparatus using a Bonse-Hart optical system to clearly capture the change in the pattern of scattered rays corresponding to the intra-planar rotation in an ultra-small angle region ($2\theta \leq 0.08°$) because a smearing phenomenon appears in the latitudinal direction. To the contrary, with an ultra-small angle X-ray scattering measuring apparatus according to the present invention, it is possible to suppress divergence (or spreading) of X-rays and, at the same time, raise the intensity of X-rays in the latitudinal direction by means of paraboloidal mirror surfaces of multilayer film. Thus, it is possible to suppress the appearance of a smearing phenomenon and clearly capture the pattern of scattered rays in an ultra-small angle region. Furthermore, the inventor of the present invention found that the appearance of the pattern of scattered rays that is captured in an ultra-small angle region changes as the sample is subjected to φ-rotation (namely intra-planar rotation) and the change is inherent in the characteristics of the substance.

When a φ-rotation system is additionally provided with an ultra-small angle X-ray scattering measuring apparatus according to the present invention and an ultra-small angle measurement is conducted while changing the intra-planar angle of the sample by means of the φ-rotation system, structures of substances may be analyzed based on various viewpoints.

Preferably, in an ultra-small angle X-ray scattering measuring apparatus according to the present invention, (1) by driving the analyzer to translate in a direction orthogonal relative to both the X-ray optical axis and the 2θ-axial line, or (2) by driving the analyzer to rotate around the axial line of the sample that extends in the direction same as that of the 2θ-axial line and is orthogonal relative to the X-ray optical axis, (3) the range of the measuring angle of the analyzer may be broadened. As a result, the 2θ-measuring range may be broadened stepwise. The inventor of the present invention has confirmed that the 2θ-measuring range was broadened up to an angle of 6° with the feature specified by the above structural elements (1)-(3).

DETAILED DESCRIPTION OF THE PREFERRED EMBODIMENTS

Figure 1:
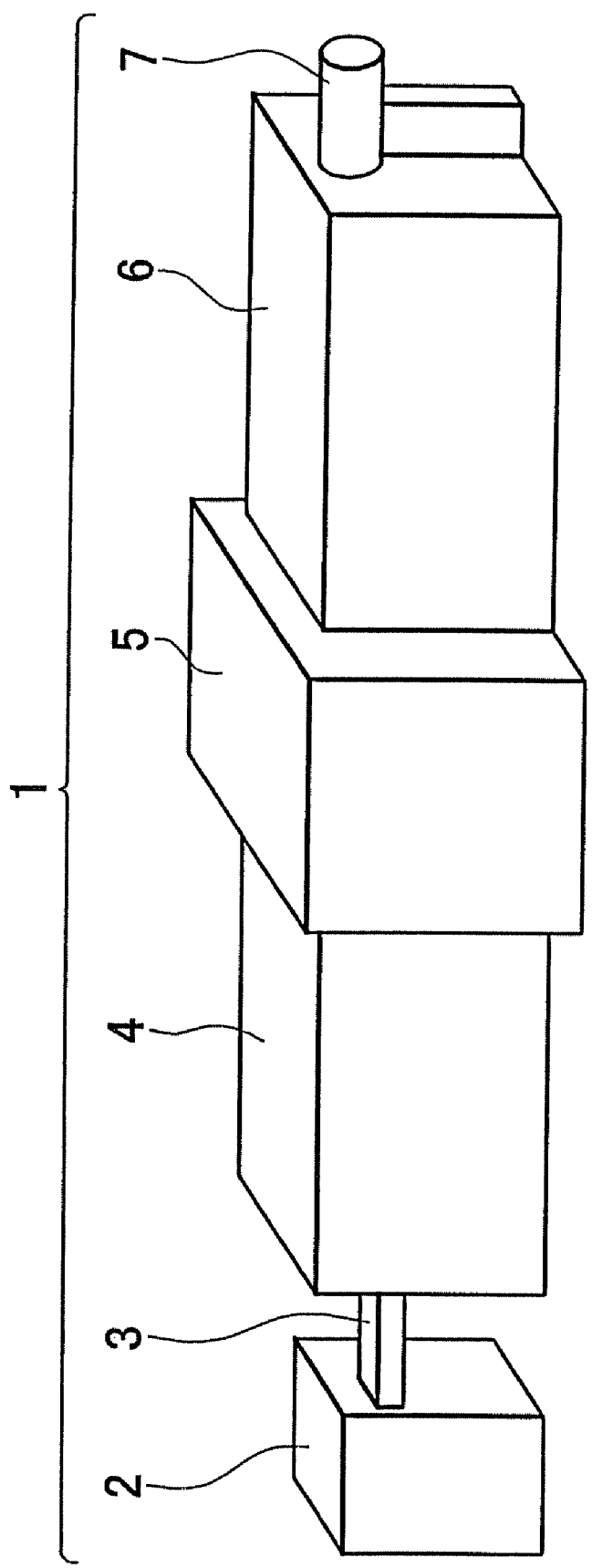
FIG. 1 is a perspective view of an appearance of an embodiment of an ultra-small angle X-ray scattering measuring apparatus according to the present invention.

Now, the present invention will be described in detail with reference of preferred embodiments of ultra-small angle X-ray scattering measuring apparatuses according to the invention, although the present invention is by no means limited to the embodiments. While the present invention is described below by referring to accompanying drawings, the components may be shown in the drawings with dimensional ratios that differ from the actual ratios for the purpose of clearly showing characteristic parts thereof.

FIG. 1 shows an embodiment of an ultra-small angle X-ray scattering measuring apparatus according to the present invention. The ultra-small angle X-ray scattering measuring apparatus 1 comprises an X-ray generator 2, an X-ray treatment chamber 3, an incidence monochromator chamber 4, a sample chamber 5, an analyzer chamber 6 and an X-ray detector 7. The X-ray optical path from the X-ray generator 2 to the X-ray detector 7 is held in vacuum or to a depressurized state that is close to vacuum by means of a decompression device (not shown).

Figure 2:
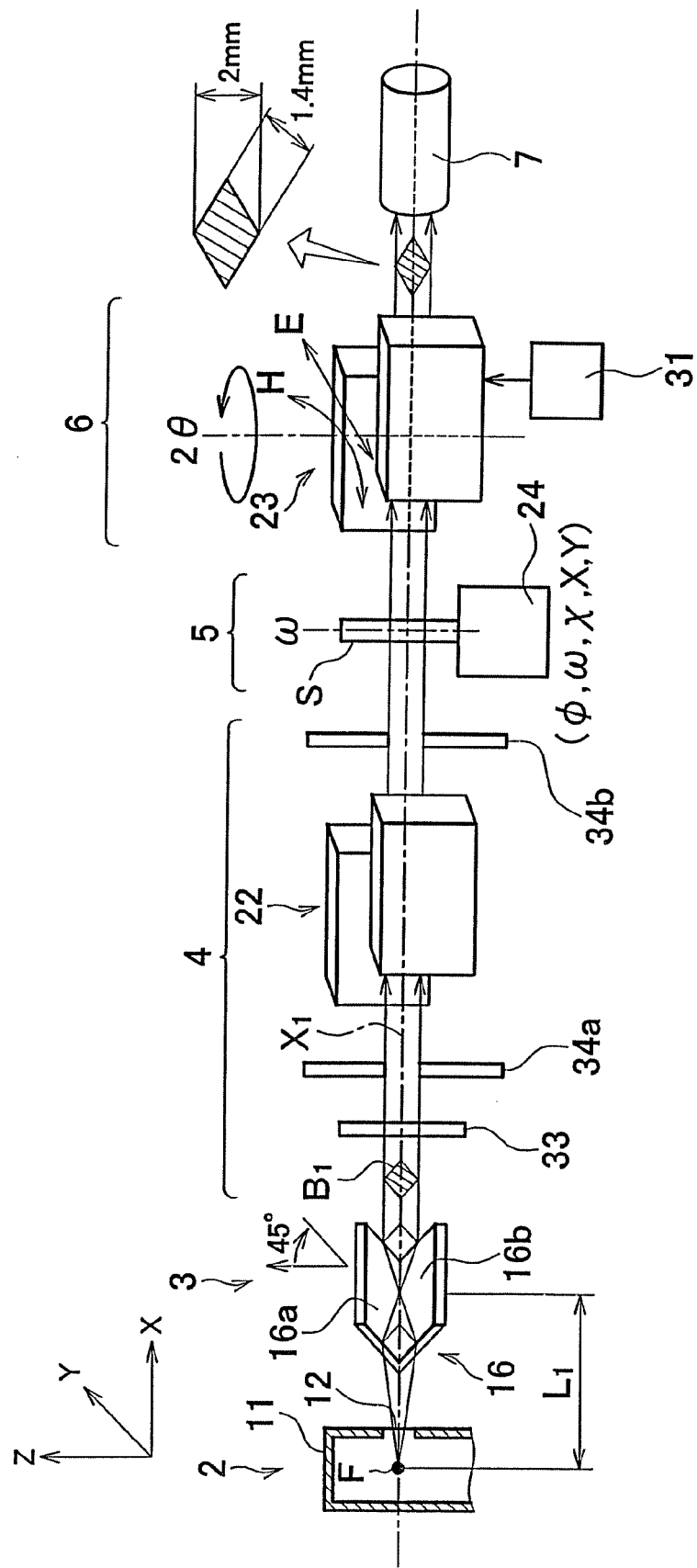
FIG. 2 is a perspective view of the ultra-small angle X-ray scattering measuring apparatus of FIG. 1 showing the internal structure thereof.

FIG. 2 shows the internal structure of the ultra-small angle X-ray scattering measuring apparatus 1 in FIG. 1. In FIG. 2, a three-dimensional space indicated by arrows X, Y and Z is took into consideration. The XY plane is a horizontal plane and the Z-direction is a vertical direction. In the case of this embodiment, the XY plane corresponds to the equatorial plane and Z-direction corresponds to the latitudinal direction. The equatorial plane contains the optical axis of X-rays directed toward a sample and also that of X-rays emitted from the sample and is orthogonal relative to the central axial line of rotation of the X-ray detector when the X-ray detector is driven to rotate and scan for detecting X-rays. The latitudinal direction is orthogonal relative to the equatorial plane.

Figure 3:
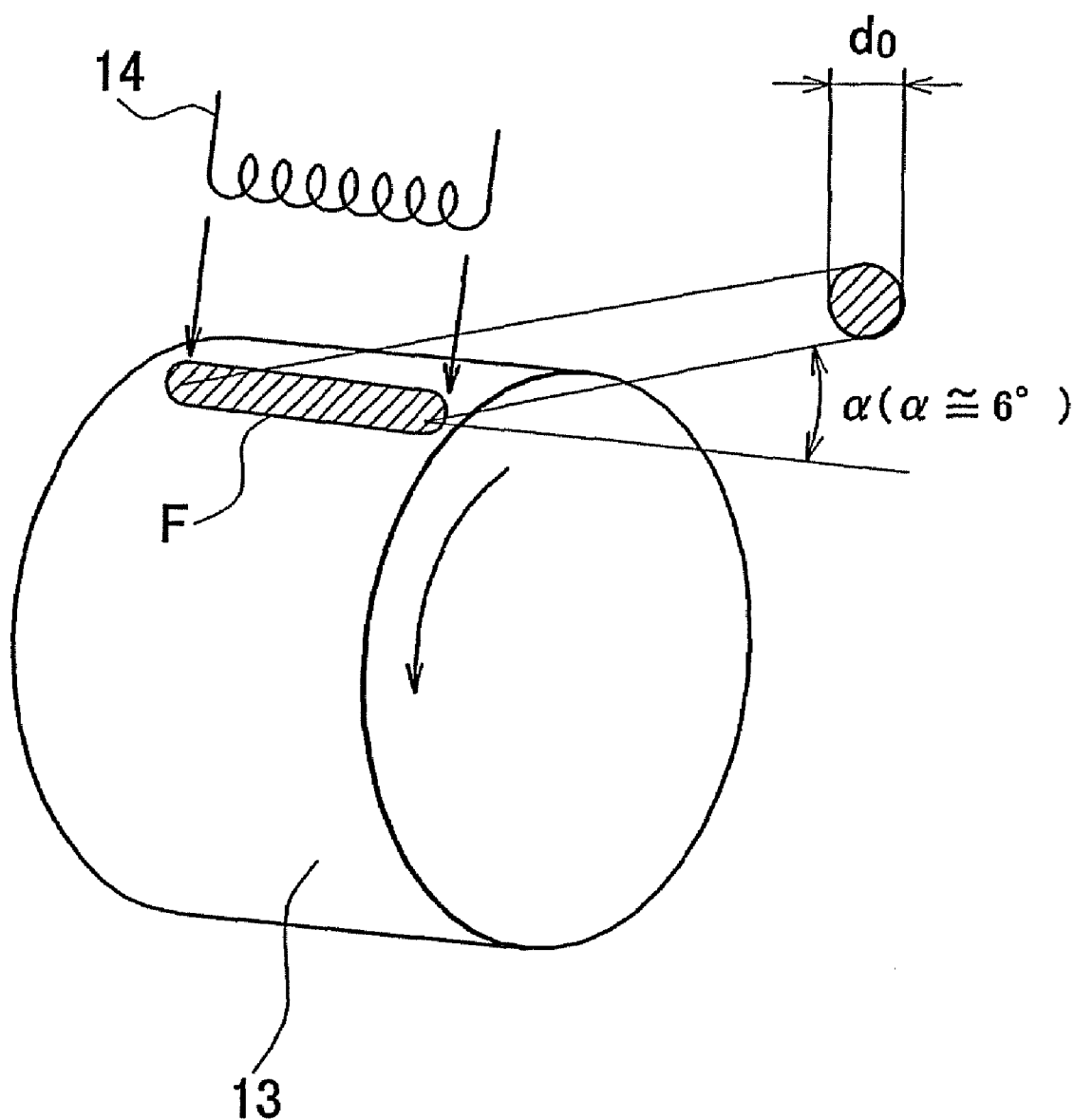
FIG. 3 is a view showing an example of an X-ray generator.

The X-ray generator 2 includes an X-ray real focus F that is the X-ray source for generating X-rays and a housing 11 that surrounds the X-ray real focus F. X-rays generated from the X-ray real focus F are taken out to the outside through an X-ray passing window 12 arranged at the housing 11. As shown in FIG. 3, the X-ray source for generating X-rays includes, for example, a rotor target (or rotating anti-cathode) 13 and a filament (or cathode) 14 disposed opposite to the rotor target 13. As the filament 14 is electrically energized, thermal electrons are emitted from the filament 14 and collide with the target 13. The region of the collision is the X-ray real focus F. Cooling water is made to flow in the inside of the target 13. The target 13 is prevented from being damaged due to the high temperature thereof by rotating the target 13 and making cooling water to flow in the inside thereof.

In this embodiment, the surface of the target 13 is formed of Cu (copper) so that the measuring operation is conducted by using characteristic X-rays of CuKα. The X-ray take-off angle α for taking off X-rays from the X-ray real focus F is 6°. The focus size $d_0$ is defined to be 0.08 mm in diameter (or 0.08 mm×0.08 mm) for an oblique viewing angle of 6°. In other words, a point-focused X-ray beam of a focus size of 0.08 mm in diameter is acquired outside of the X-ray generator 2. Referring to FIG. 2, X-rays taken out from the X-ray real focus F are taken into the X-ray detector 7 by way of the X-ray treatment chamber 3, the incidence monochromator chamber 4, the sample chamber 5 and the analyzer chamber 6. The central axial line of the X-ray optical path from the X-ray real focus F to the X-ray detector 7 is referred to as X-ray optical axis $X_1$. When the proceeding direction of X-rays emitted from the X-ray real focus F is made to change by some optical element, the X-ray optical axis $X_1$ changes according to the change in the proceeding direction of X-rays.

Figure 4A:
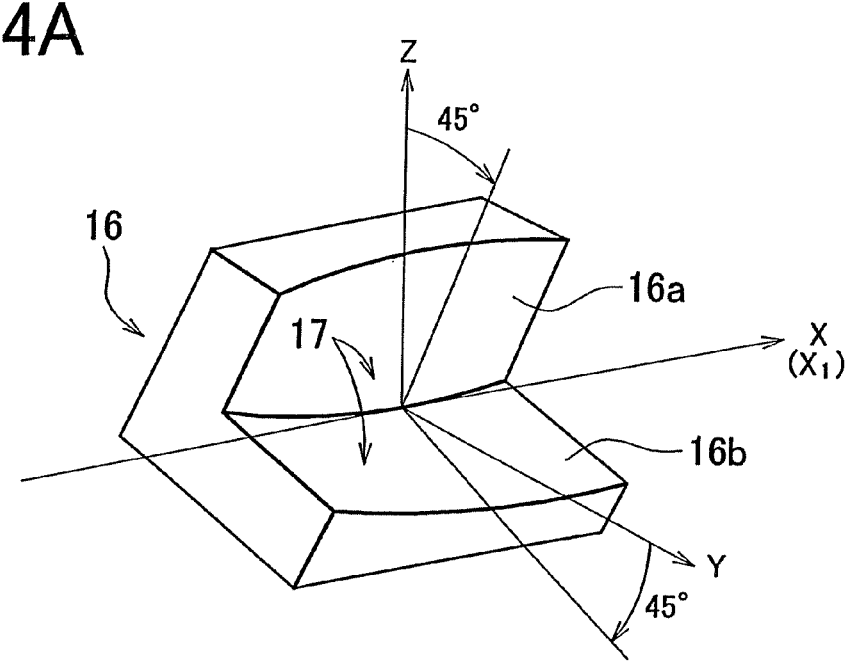
FIGS. 4A, 4B and 4C are views of an example of an X-ray collimating mirror, FIG. 4A showing an appearance thereof, FIG. 4B showing the structure of the internal multilayer film thereof, and FIG. 4C showing a characteristics of spread of X-rays.
Figure 4B:
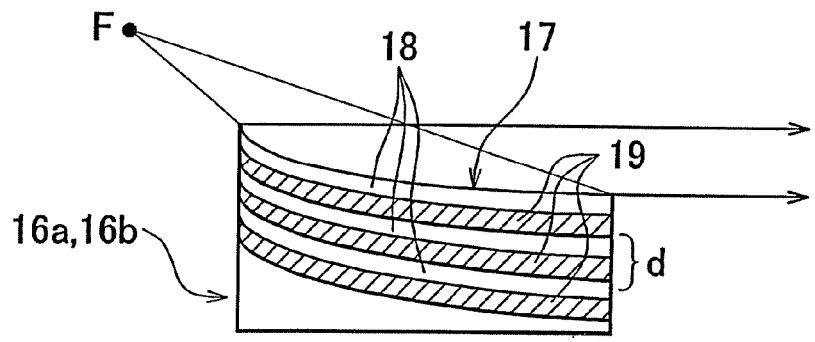

An X-ray collimating mirror 16 is arranged in the inside of the X-ray treatment chamber 3. As shown in FIG. 4A, the X-ray collimating mirror 16 is formed by using a pair of X-ray reflection mirrors including a first mirror 16a and a second mirror 16b that are arranged orthogonally relative to and bonded to each other. As shown in FIG. 4B, X-ray reflection surfaces 17 of the first mirror 16a and the second mirror 16b are paraboloidal. Additionally, each of the X-ray reflection surfaces 17 is formed by a multilayer structure of a heavy element 18 and a light element 19. Although only three layer pairs of a heavy element layer 18 and a light element layer 19 are illustrated in FIG. 4B, hundreds to thousands layer pairs are actually arranged.

The heavy element of the heavy element layers 18 may typically be selected from tungsten (W), platinum (Pt) and nickel (Ni). The light element of the light element layers 19 may typically be selected from carbon (C) and silicon (Si). In this embodiment, nickel is used for the heavy element while carbon is used for the light element. By using a combination of nickel and carbon, it is possible to produce very intense parallel X-rays that are suitable for ultra-small angle X-ray scattering measuring operations.

As X-rays generated from the X-ray real focus F enter the mirrors 16a and 16b, the X-rays are diffracted by the sample if the following well known Bragg's condition of diffraction, $$2d \times \sin\theta = n\lambda$$

is met between the X-rays and the sample, where "λ" is the wavelength of X-rays, "θ" is the angle of incidence of X-rays, "d" is the interplanar spacing of lattice planes that correspond to the thickness of the layer pairs 18 and 19, and "n" is the reflection order.

In this embodiment, the interplanar spacing of lattice planes d that is produced by the layer pairs 18 and 19 is formed so as to continuously change along the paraboloidal surfaces 17 in order to meet the Bragg's condition at any arbitrarily selected position on the X-ray reflection surfaces 17 relative to a specific wavelength such as that of CuKα rays. Such a multilayer film can be prepared, for instance, by means of the method disclosed in Japanese Patent Laid-Open Publication No. 60-7400. Since the X-ray reflection surfaces 17 of the mirrors 16a and 16b are formed by a plurality of layer pairs 18 and 19 that can diffract X-rays at any point thereof, X-rays radiated from the X-ray real focus F and diffracted by the X-ray reflection surfaces 17 are emitted from the mirrors 16a and 16b as a parallel X-ray beam. Additionally, since such parallel X-rays are produced from each of the layer pairs of the multilayer films, the X-rays show a very strong (or high) intensity.

Referring to FIG. 4A, X-rays that enter the first mirror 16a and the second mirror 16b are alternately and repeatedly reflected by the mirrors 16a and 16b, and then they are emitted as a parallel X-ray beam. Since the first mirror 16a and the second mirror 16b are arranged orthogonally relative to each other, the emitted X-ray beam shows a rhombic cross section as indicated by reference symbol $B_1$ in FIG. 2. In other words, the X-ray beam is two-dimensionally collimated.

The first mirror 16a and the second mirror 16b are inclined respectively relative to the vertical axis (Z-axis) and the horizontal axis (Y-axis) by an angle of 45°. Therefore, the rhombic cross section $B_1$ of the X-ray beam is a rhombus having diagonals in the direction of the intra-equatorial-plane (XY plane) and in the vertical direction Z. The X-ray collimating mirror 16 is inclined by an angle of 45° in order to make it easy to take out a beam of parallel X-rays into the equatorial plane (XY plane). When the X-ray collimating mirror is used without being inclined, firstly the reflected beam is emitted in a direction inclined relative to the equatorial direction by 45°. Secondly, when a reflection mirror in the longitudinal direction (inclined by 90°) and a reflection mirror in the transversal direction (inclined by 0°) are separated from each other and the first time reflection is used for each of them, the solid angle of striking the reflection mirrors becomes small to make it impossible to raise the intensity and the angle of divergence becomes large in the latitudinal direction to make X-rays of the incident beam poorly parallel. Thus, it is preferable that the X-ray collimating mirror 16 is inclined by 45° for operation to dissolve these problems.

Each individual X-ray beam in the parallel X-rays emitted from each of the first mirror 16a and the second mirror 16b of the X-ray collimating mirror 16 has a spreading angle $\delta_0$. The spreading angle $\delta_0$ is given as the peak width of the rocking curve, or generally as the full width at half maximum intensity (or FWHM) thereof, when the rocking curve has been observed for the paraboloidal multilayer mirrors 16a and 16b. In an experiment conducted by using this embodiment where the layer pairs of the multilayer film is formed by using nickel and carbon as heavy element and light element respectively, it was found that the spreading angle $\delta_0$ due to the mirrors 16a and 16b themselves is about 0.04°.

While the spreading angle $\delta_0$ of the X-ray beam due to the mirrors 16a and 16b themselves is about 0.04°, the spreading angle of the X-ray beam due to the X-ray collimating mirror 16 in actual operations is $$0.04 \times (1/\sin 45°) = 0.057 (= \text{about } 0.06°)$$

, because the X-ray collimating mirror 16 is inclined by 45° for operations in this embodiment. Thus, the beam of two-dimensionally parallel X-rays emitted from the X-ray collimating mirror 16 in FIG. 2 is in fact formed by an ensemble of beams, each of which disperses with a spreading angle of about 0.06° in the Y-direction and the Z-direction.

The point-focused X-rays generated by the X-ray real focus F and taken out with a focus size of 0.08 mm in diameter are then taken in from the X-ray entering port of the X-ray collimating mirror 16 while they are spreading in angle. Note that X-rays do not show a sufficient intensity when the size of the cross section of the spreading X-rays is too small relative to the area of the aperture of the X-ray entering port of the X-ray collimating mirror 16, whereas X-rays coming out from the X-ray real focus F are wasted to a large extent when the size of the cross section of the spreading X-rays is too large relative to the area of the aperture of the X-ray entering port of the X-ray collimating mirror 16. In this embodiment, the distance $L_1$ from the X-ray real focus F to the center of the X-ray collimating mirror 16 is defined to be about 125 mm (meaning 85 mm to the X-ray entering port) and the X-ray entering port is defined to be 1.3 mm×1.3 mm so that X-rays coming out from the X-ray real focus F are taken into the X-ray collimating mirror 16 without being wasted in order to obtain a parallel X-ray beam showing a very strong intensity.

Referring to FIG. 2, an incidence monochromator 22 is arranged in the incidence monochromator chamber 4. The sample S that is the object of observation is arranged in the sample chamber 5 and supported by a sample support device 24. An analyzer 23 is provided in the analyzer chamber 6. The incidence monochromator 22 operates to turn X-rays entering the sample S to monochromatic and collimate them in the equatorial plane (XY plane). X-rays are collimated in the equatorial plane to control divergence (spreading, or dispersion) of X-rays in the equatorial plane. The analyzer 23 operates to select particular wavelength components from scattered rays generated from the sample S and direct them toward the X-ray detector 7.

Figure 5A:
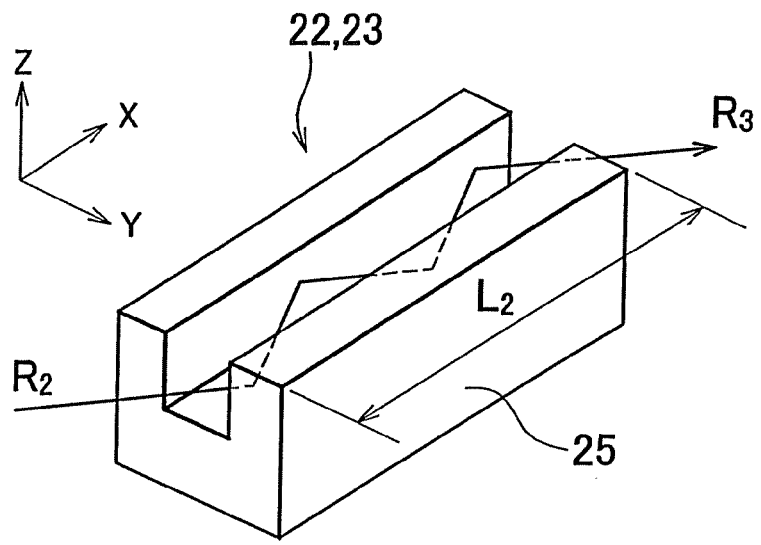
FIGS. 5A and 5B are views of an example of a monochromator and an analyzer, FIG. 5A showing an appearance thereof, and FIG. 5B showing a characteristics of spread of X-rays.

Both the monochromator 22 and the analyzer 23 are formed by using a channel-cut crystal 25 as shown in FIG. 5A. A channel-cut crystal 25 is prepared typically by forming a groove on a block of perfect crystal of germanium. The opposite lateral surfaces of the groove produced by cutting the block operate as X-ray reflection surfaces. Crystal lattice planes of germanium single crystal are arranged in parallel with each other on each of the X-ray reflection surfaces with a predetermined interplanar spacing of lattice planes. X-rays $R_2$ that enter the channel-cut crystal 25 are reflected by the pair of X-ray reflection surfaces for a plurality of times, e.g., four times, and exit as X-rays $R_3$ that are parallel in the XY plane. The length L2 of the channel-cut crystal 25 is selected such that X-rays can be reflected four times on the X-ray reflection surfaces. Note, however, that the number of times of reflections of X-rays on the X-ray reflection surfaces is not limited to four times and may alternatively be twice or some other number of times.

Figure 4C:
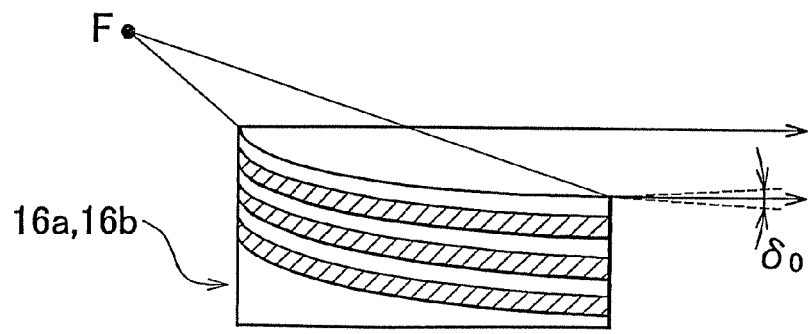
Figure 5B:
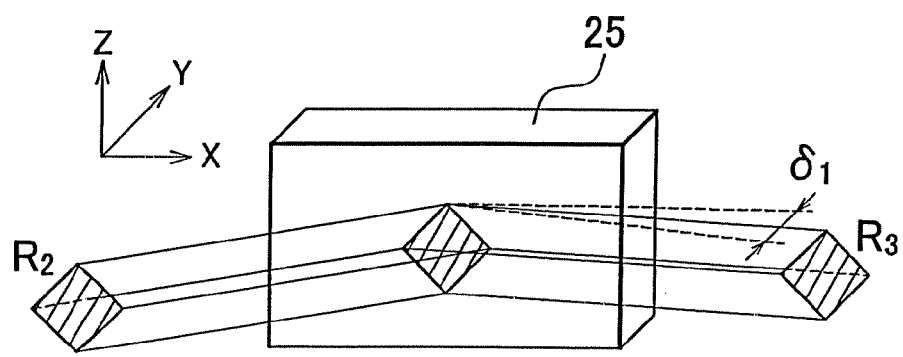

In this embodiment, a parallel X-ray beam having a rhombic cross section enters the monochromator 22 and the analyzer 23 as shown in FIG. 2. The parallel X-ray beam having a rhombic cross section that strikes the X-ray reflection surfaces of the channel-cut crystals 25 of the monochromator 22 and the analyzer 23 is controlled against divergence (or dispersion) in the XY plane so as to be collimated and turned to monochrome at the same time as shown in FIG. 5B. The spreading angle $\delta_1$ in the XY plane of the individual beams that constitute the outgoing beam $R_3$ was measured in an experiment by observing the rocking curve as the full width at half maximum intensity (or FWHM) of the rocking curve. As a result, the spreading angle $\delta_1$ was approximately 0.00°. Since a channel-cut crystal 25 does not function to control divergence (or dispersion) of X-rays in the Z-direction, the spreading angle of the collimated X-ray beam $R_3$ emitted from the channel-cut crystal 25 is exactly the spreading angle itself in the Z-direction of the X-ray beam entering the channel-cut crystal 25. The spreading angle in the Z-direction is exactly the spreading angle $\delta_0$ itself that is controlled by the X-ray collimating mirror 16 of FIG. 2 (see FIG. 4C). In this embodiment, $\delta_0$=about 0.06° as pointed out above.

As may be clear from the above description, X-rays that enter the sample S in FIG. 2 are highly accurately collimated by the X-ray collimating mirror 16 and the monochromator 22 in the two-dimensional directions of the intra-equatorial-plane (XY plane) and the latitudinal direction. More specifically, the angle of divergence (or dispersion) in the intra-equatorial-plane is controlled to about 0.002° and the angle of divergence (or dispersion) in the latitudinal direction (Z-direction) is controlled to about 0.06°.

Figure 6A:
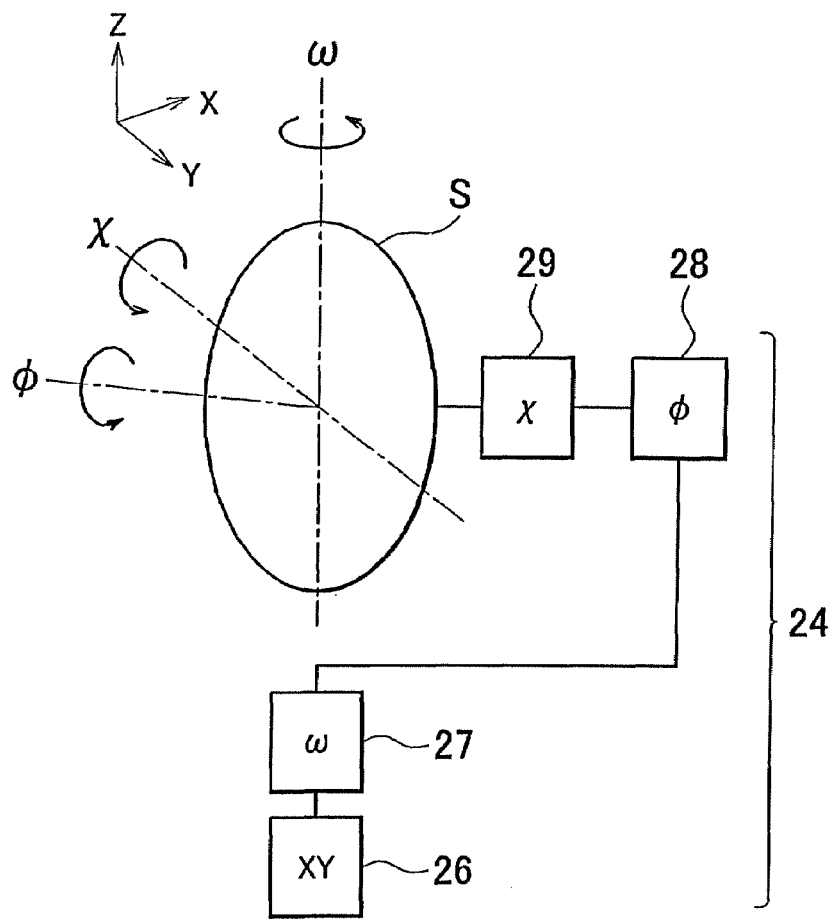
FIG. 6A is a view showing an example of a whole sample-support device and FIG. 6B is a view illustrating one of functional features thereof.

The sample S is supported by the sample support device 24 in the sample chamber 5. As shown in FIG. 6A, the sample support device 24 includes an XY stage 26, an ω-rotary system 27, a φ-rotary system 28 and a χ-rotary system 29. The sample S is supported by the χ-rotary system 29, which is mounted on the ω-rotary system 28. The p-rotary system 28 is mounted on the φ-rotary system 27, which is then mounted on the XY stage 26.

Of the above rotary systems, the ω-rotary system has a relationship of ω/2θ with the analyzer crystal 23 so that it is required of a precision level of 0.0001°. The rotary systems other than the ω-rotary system are required of a precision level of 0.01°. A rotary system that is required of a high precision level such as the ω-rotary system may be realized by using an appropriate micro-rotary drive mechanism such as a tangent bar type drive mechanism. The drive source is preferably a position-controllable electric motor such as a pulse motor or a servomotor. The XY stage 26 can be realized by a known plane parallel translation mechanism such as a combination of a feed screw shaft that is driven to rotate by a position-controllable electric motor and a slide member that is held in thread-engagement with the feed screw shaft.

The ω-rotary system 27 shifts the angular position of the sample S around the ω-axial line, which is an axial line that extends in the Z-direction and does not move. The rotating movement of the sample S around the ω-axial line is referred to as ω-rotation hereinafter. The φ-rotary system 28 shifts the angular position of the sample S around the φ-axial line that intersects (or transmits) the sample S. The φ-axial line is an axial line that shows a rotating movement according to an ω-rotation of the sample S. The rotating movement of the sample S around the φ-axial line is referred to as φ-rotation or intra-planar rotation hereinafter. The χ-rotary system 29 shifts the angular position of the sample S around the χ-axial line that passes through the surface of the sample S. The χ-axial line is an axial line that shows a rotating movement according to an ω-rotation and a φ-rotation of the sample S. The rotating movement of the sample S around the χ-axial line is referred to as χ-rotation, inclined movement or fanning movement hereinafter.

Figure 6B:
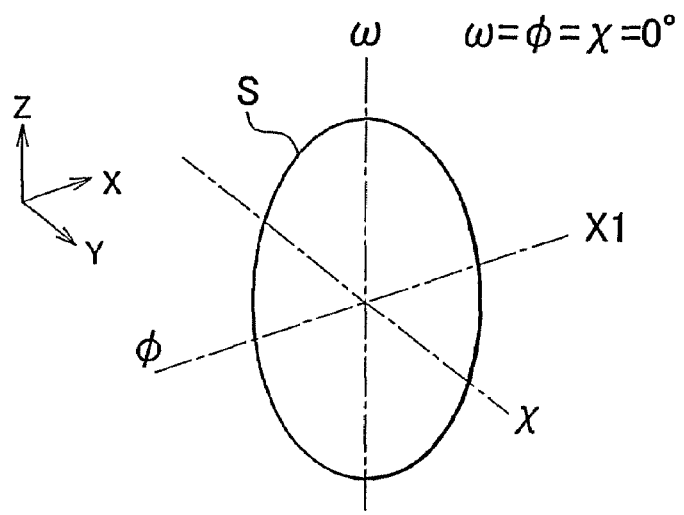
Figure 7A:
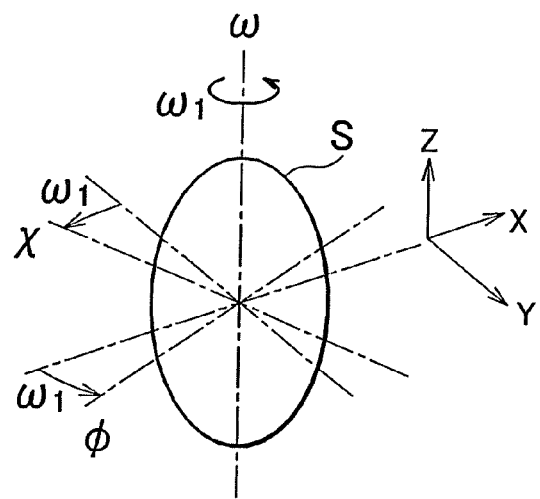
FIGS. 7A, 7B and 7C are views illustrating functional features of the sample-support device of FIG. 6A.

Assume here that the ω-axial line extends in the Z-direction and the φ-axial line extends in the X-direction and agrees with the X-ray optical axis $X_1$ in case ω=0, φ=0, and χ=0 as shown in FIG. 6B, whereas the χ-axial line orthogonally intersects the ω-axial line and the φ-axial line as shown in FIG. 6B. As the sample S is driven to rotate for ω-rotation around the ω-axial line from 0° to $ω_1$ in this state, the sample S shows an ω-rotation of angle $ω_1$ around the ω-axial line, while both the φ-axial line and the χ-axial line are driven to rotate around the ω-axial line by angle $ω_1$ as shown in FIG. 7A.

Figure 7B:
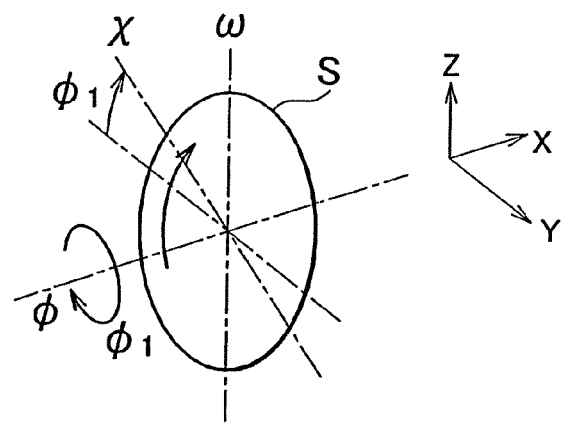
Figure 7C:
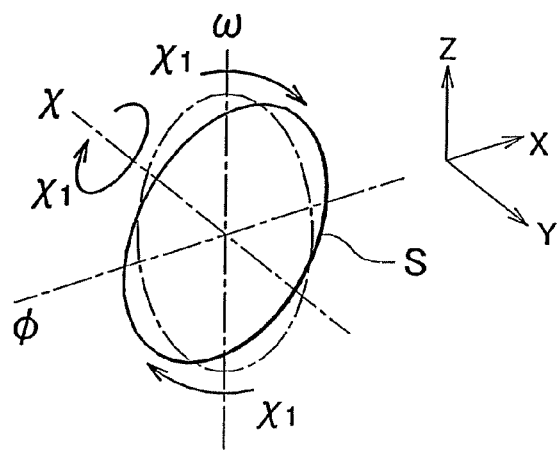

Similarly, as the sample S is driven to rotate for φ-rotation around the φ-axial line from 0° to $φ_1$ in the state of ω=φ=χ=0 (the state of FIG. 6B), the sample shows a φ-rotation of angle $φ_1$ around the p-axial line but the ω-axial line does not shift, while the χ-axial line is driven to rotate around the φ-axial line by angle $φ_1$ as shown in FIG. 7B. Finally, as the sample S is driven to rotate for χ-rotation around the χ-axial line by angle $χ_1$ in the state of ω=φ=χ=0 (the state of FIG. 6B), the sample S shows a χ-rotation of angle $χ_1$ around the χ-axial line but both the ω-axial line and the φ-axial line do not move as shown in FIG. 7C.

In the inside of the analyzer chamber 6 shown in FIG. 2, the analyzer 23 made of a channel-cut crystal of germanium is supported by an analyzer support device 31 and arranged at a predetermined position on the X-ray optical axis $X_1$. The analyzer support device 31 drives the analyzer 23 for rotational movement around the 2θ-axial line that orthogonally intersects the X-ray optical axis $X_1$ and extends in the vertical direction (Z-direction). As a result of the rotational movement, it is possible to shift the angular position of the analyzer 23 around the 2θ-axial line. The above angular position of the analyzer 23 is referred to as 2θ-angular position and the rotation of the analyzer 23 around the 2θ-axial line is referred to as 2θ-rotation hereinafter. The 2θ-direction is an intra-equatorial-plane (XY plane) direction.

The analyzer support device 31 has a function of driving the analyzer 23 for rotational movement around the 2θ-axial line along with a function of driving the analyzer 23 for translation in a direction orthogonal relative to the X-ray optical axis $X_1$ as indicated by arrow E, or a function of driving the analyzer 23 for rotational movement around the ω-axial line that passes through the sample S as indicated by arrow H. The translation in the direction E or the rotational movement in the direction H is for changing the detection range of scattered rays by the analyzer 23 stepwise in order to broaden the detection range of scattered rays by the analyzer 23.

Thus, it is possible to detect scattered rays from crystal particles that are present in the sample S by detecting X-rays by means of the X-ray detector 7, while driving the sample S to translate and/or rotate by means of the sample support device 24 and also driving the analyzer 23 for rotational movement around the 2θ-axial line by means of the analyzer support device 31.

Figure 8:
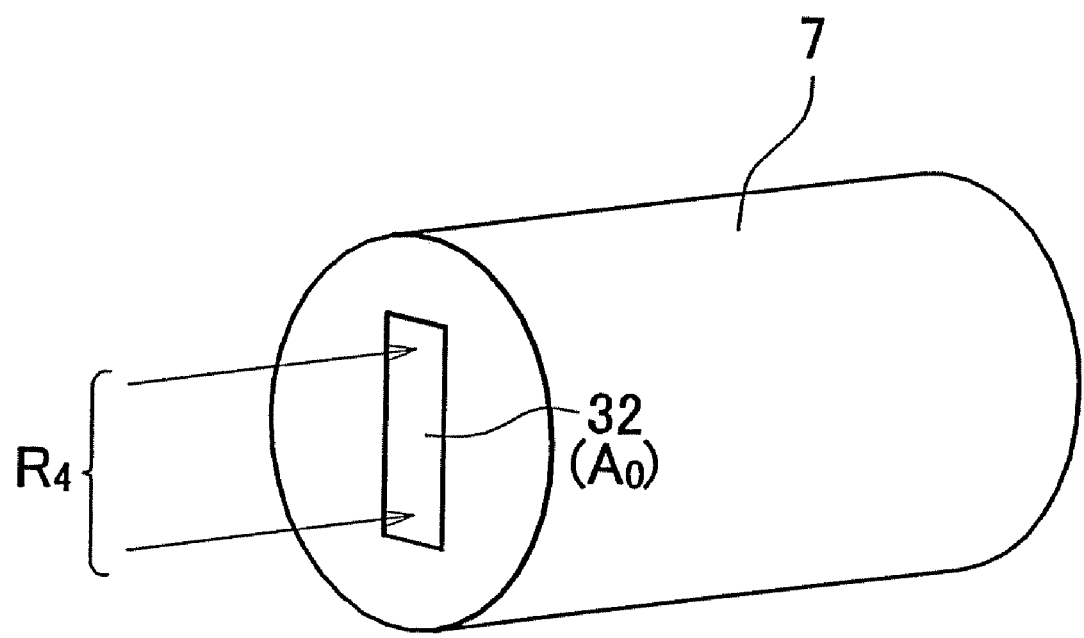
FIG. 8 is a perspective view of an example of X-ray detection device.

The X-ray detector 7 is a zero-dimensional X-ray detector, which is typically an SC (scintillation counter). It is well known that an SC has an X-ray intake port 32 of an appropriate area as shown in FIG. 8. The region for taking in X-ray $R_4$ by way of the X-ray intake port 32 is the X-ray detection region $A_0$. The X-ray detector 7 does not show any positional resolution and outputs the sum or the integral of the X-rays taken in through the X-ray intake port 32 as a single X-ray intensity signal. In this embodiment, the cross section of X-rays immediately before being taken in by way of the X-ray intake port 32 is rhombic with the diagonal distance of about 2 mm and the length of each side of about 1.4 mm as shown in FIG. 2. On the other hand, the sensitive window size of the X-ray intake port 32 is 1 inch (namely 25.4 mm) in diameter.

Referring to FIG. 2, an attenuator 33 is arranged on the X-ray optical axis $X_1$ behind the X-ray collimating mirror 16. The attenuator 33 is an X-ray optical element that is also referred to as absorber. The attenuator 33 attenuates the intensity of X-rays produced from the X-ray real focus F by means of a substance that can absorb X-rays. Substances that can be used for absorbing X-rays for the purpose of the present invention include Al (aluminum). Normally, an aluminum plate is selected from a plurality of aluminum plates having different thickness and placed on the X-ray optical axis X1 to attenuate X-rays with a desired attenuation factor. Such an attenuator 33 is used to attenuate the X-rays because the 2θ-measuring region of the ultra-small angle X-ray scattering measuring apparatus of this embodiment is typically an angular region not greater than 0.08° and the intensity of the direct beam in this angular region needs to be suppressed.

Four-quadrant slits 34a and 34b are arranged on the X-ray optical axis $X_1$ respectively in front and at the back of the incidence monochromator 22. A four-quadrant slit is a slit whose slit width can be adjusted in four directions, that is, transversely two directions (in the Y-direction) and vertically two directions (in the Z-direction). The four-quadrant slit 34a arranged upstream relative to the monochromator 22 can cut out the first time reflection and other unnecessary reflections that are produced by the X-ray collimating mirror 16 and take in only the second time reflection that is necessary. On the other hand, the four-quadrant slit 34b arranged downstream relative to the monochromator 22 can cut out Kα2 rays and take in only Kα1 rays.

Now, the measuring operation of the ultra-small angle X-ray scattering measuring apparatus having the above-described configuration will be described below by way of a specific example. A piece of substance containing a cluster of a structure of 200 nm to 1 μm (an aggregate of atoms and molecules) is set on the X-ray optical axis $X_1$ by the sample support device 24 as sample S inside the sample chamber 5 shown in FIG. 2. The sample support device 24 is operated to drive the sample S for XY translation, ω-rotation, φ-rotation and/or χ-rotation, if necessary, and set the sample S to take a desired posture.

Then, X-rays are generated from the X-ray real focus F in the X-ray generator 2, and then generated X-rays are two-dimensionally collimated to form a parallel X-ray beam having a rhombic cross section. The sample S is irradiated with such collimated X-rays. The incident X-rays are X-rays that are highly precisely two-dimensionally collimated by the X-ray collimating mirror 16, which is a multilayer paraboloidal mirror, and show a very strong intensity, and further turned to monochromatic and highly precisely collimated by the monochromator 22.

As the flux of parallel X-ray emitted from the monochromator 22 is incident on the sample S, scattered rays are produced in the ultra-small angle region (2θ≦0.08°) according to the characteristics of the sample S. The necessary ones of the scattered rays are selectively picked up by the analyzer 23 and measured by the X-ray detector 7 for the intensity of the selected scattered rays. The measuring operation is conducted in a predetermined angular range, while intermittently changing the angle around the 2θ-axial line of the analyzer 23 stepwise with an appropriate step width, or continuously changing at a predetermined rotational angular velocity. It is possible to drive the analyzer 23 to translate in the direction of arrow E by a predetermined distance or rotate around the ω-axial line in the direction of arrow H by a predetermined angle to broaden the range of detection angle of the analyzer 23 for detecting scattered rays. In an experiment conducted by the inventor of the present invention, it was possible to broaden the detection range up to 2θ=6° by moving the analyzer 23 stepwise.

Figure 9A:
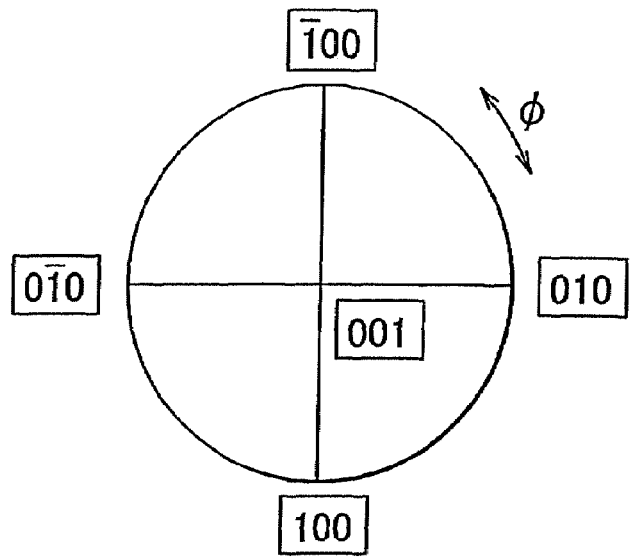
FIG. 9A is a view illustrating an example of crystal structure in a sample.
Figure 9B:
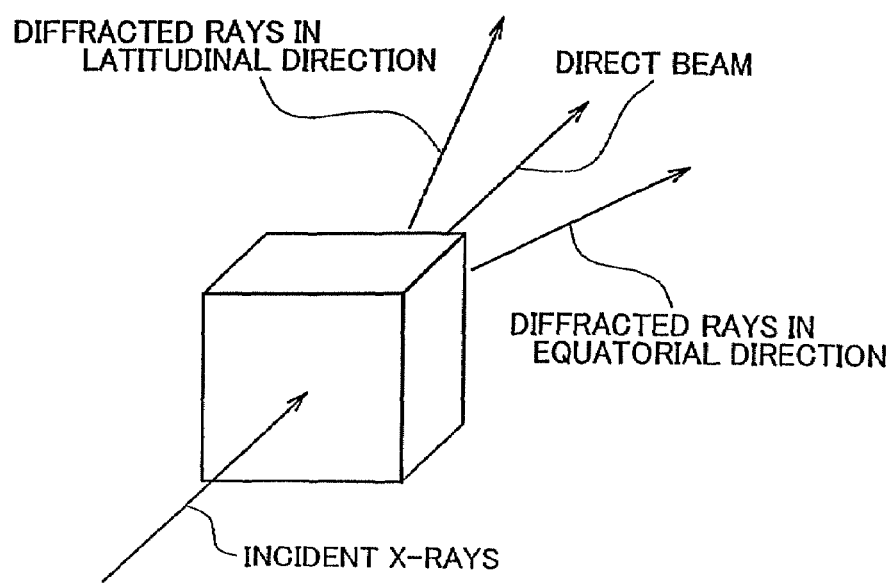
FIG. 9B is a schematic illustration of X-ray diffraction through the crystal.
Figure 10:
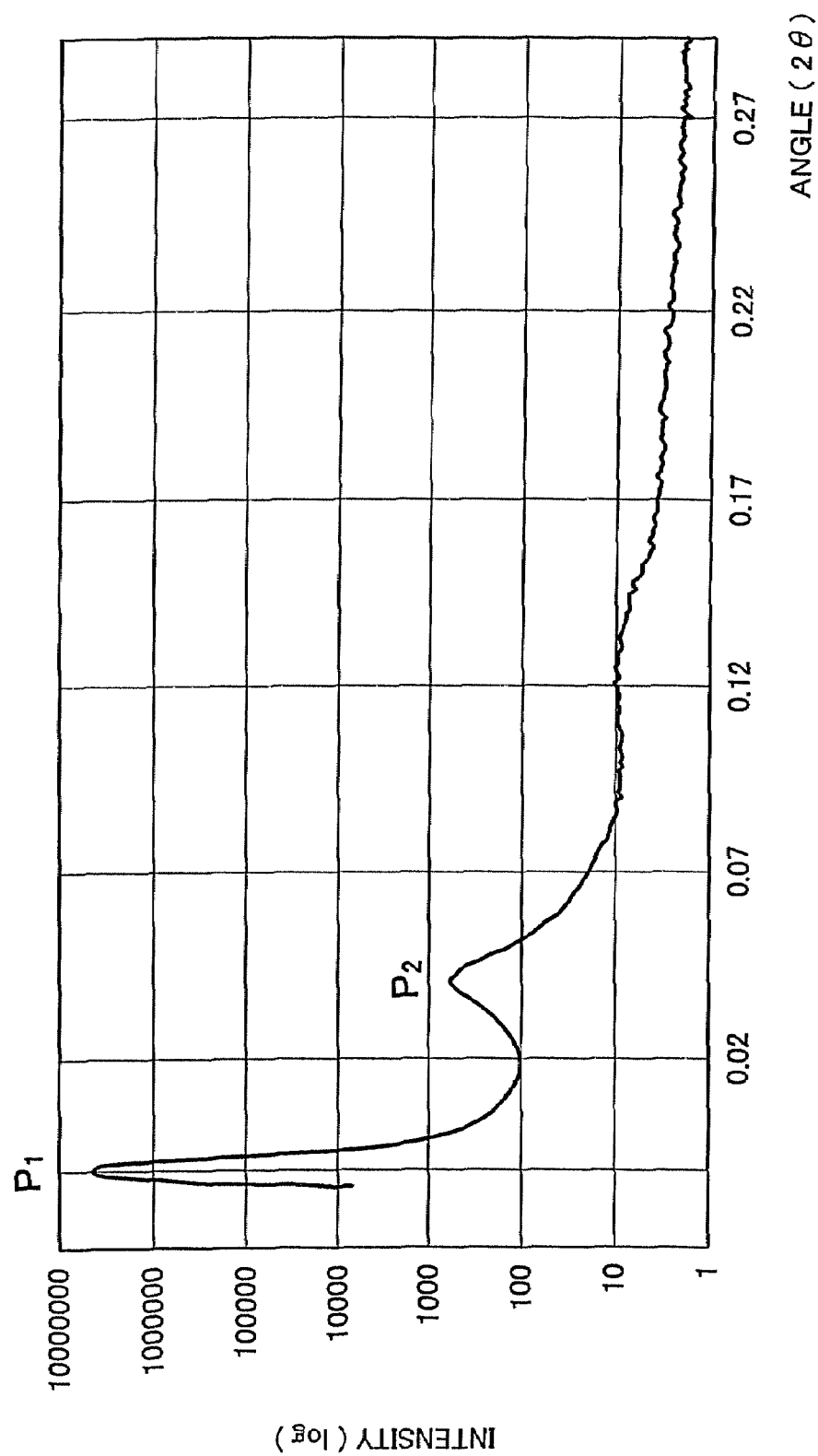
FIG. 10 is one of graphs of results of measurements.
Figure 11:
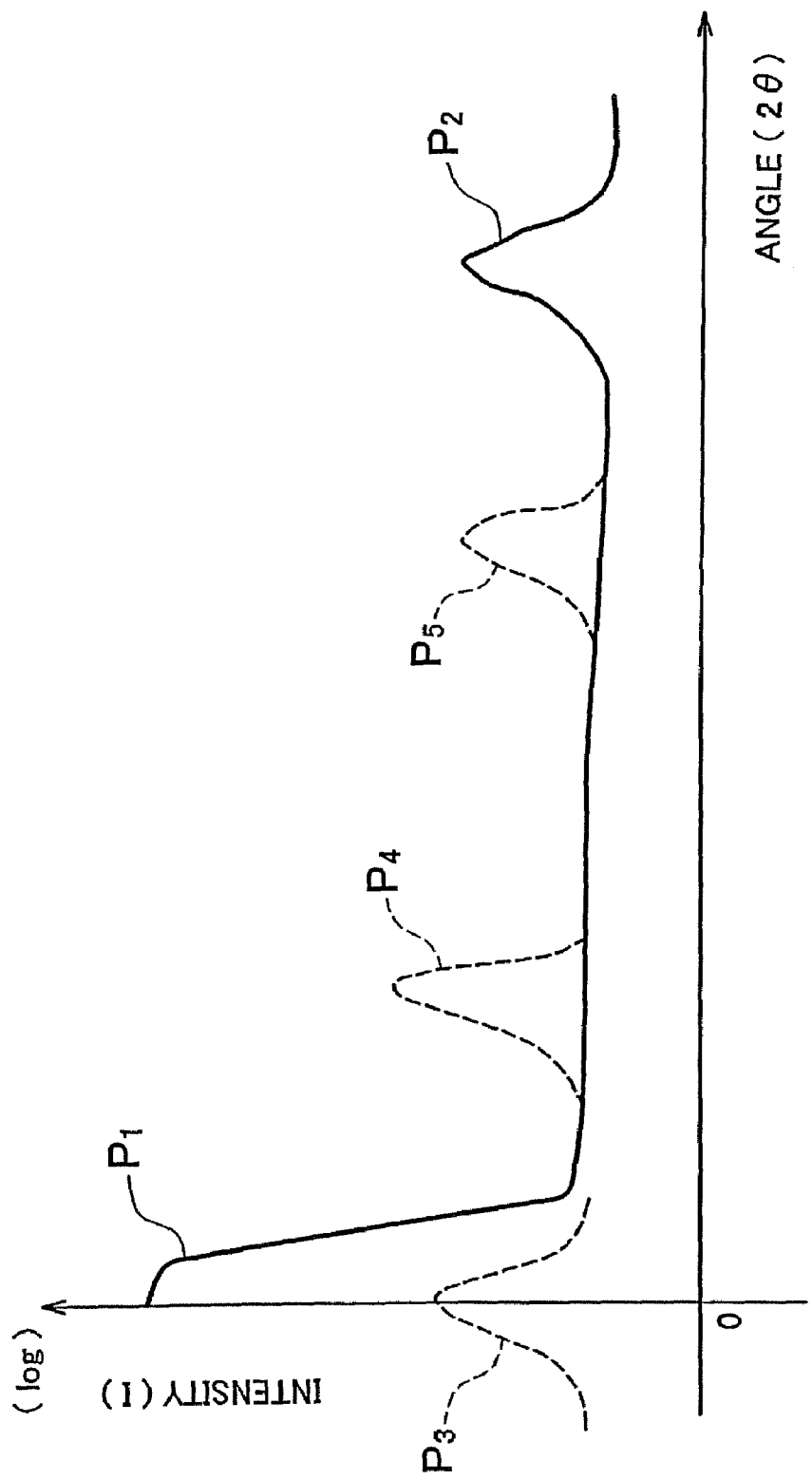
FIG. 11 is an illustration of part of the graph of FIG. 10, showing it in detail.
Figure 12A:
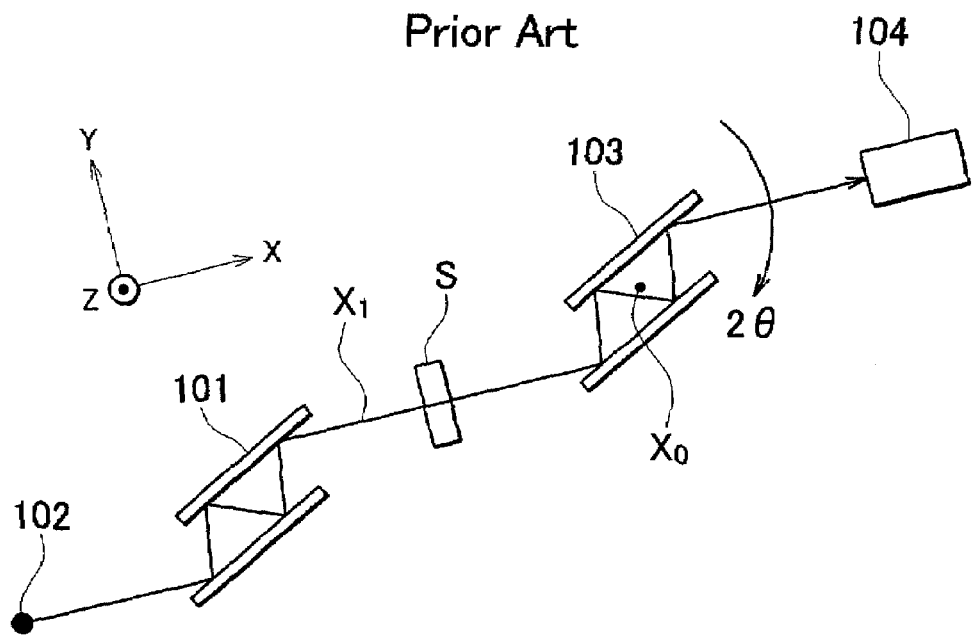
FIG. 12A is a view showing an example of a known ultra-small angle X-ray scattering measuring apparatus as a whole.
Figure 12B:
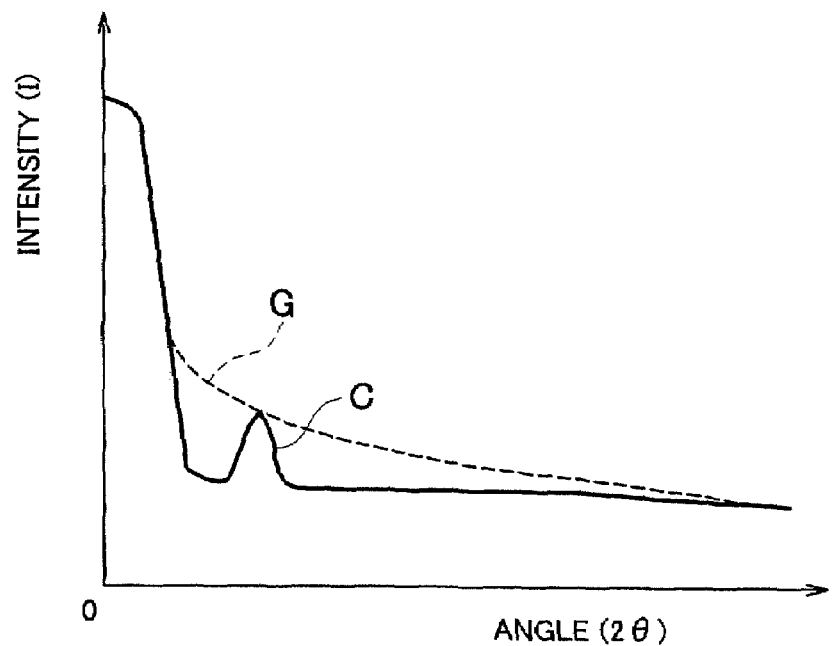
FIG. 12B is one of graphs of results of measurements using the device of FIG. 12A.

As a result of the above-described measuring operation, it is possible to obtain results typically as shown in FIG. 10. In FIG. 10, the peak $P_1$ that appears near 2θ=0° is the peak of the direct beam. The peak $P_2$ represents diffracted rays (namely scattered rays) by (010) plane in intra-equatorial-plane directions when the intra-planar rotational angle φ=0° (e.g., when incident X-rays and the crystal are in the state shown in FIG. 9B). Both the peak $P_1$ and the peak $P_2$ appear in the direct beam. FIG. 11 is an enlarged view of the angular region from the peak $P_1$ to the peak $P_2$ in FIG. 10. In FIG. 11, the peak $P_4$ and the peak $P_5$ are peaks that appear when the intra-planar angle φ of the sample is rotated clockwise by a certain angle for 2θ-measuring. The peak $P_4$ is caused by (−100) plane in FIG. 9A, whereas the peak $P_5$ is caused by (010) plane.

The peak $P_3$ represents diffracted rays in the latitudinal direction when φ=0°, but the peak $P_3$ cannot be observed because it is overlapped with the peak of the direct beam. For example, the intensity of the direct beam is about 6 million cps, whereas the intensity of the peak $P_3$ is about tens to hundreds of several cps. The direct beam is attenuated to 1/64 by the Al (aluminum) attenuator. Since the difference of intensity is large and the intensity of the peak $P_3$ is less than that of noises near the direct beam, it is impossible to detect the peak $P_3$. Additionally, since the peak $P_3$ shows a profile that is similar to the direct beam, it is impossible to discriminate the peak $P_3$ from the direct beam if the intensity of the peak $P_3$ is boosted to the level of noises.

By comparing apparatus of the prior art optical system where X-rays entering the sample are turned to monochromatic and collimated simply by means of a monochromator 22 without using an X-ray collimating mirror 16 as shown in FIG. 2 as in the case of a conventional Bonse-Hart optical system and the optical system of this embodiment, it will be seen that this invention provides the advantages (1) through (5) listed below.

Figure 13A:
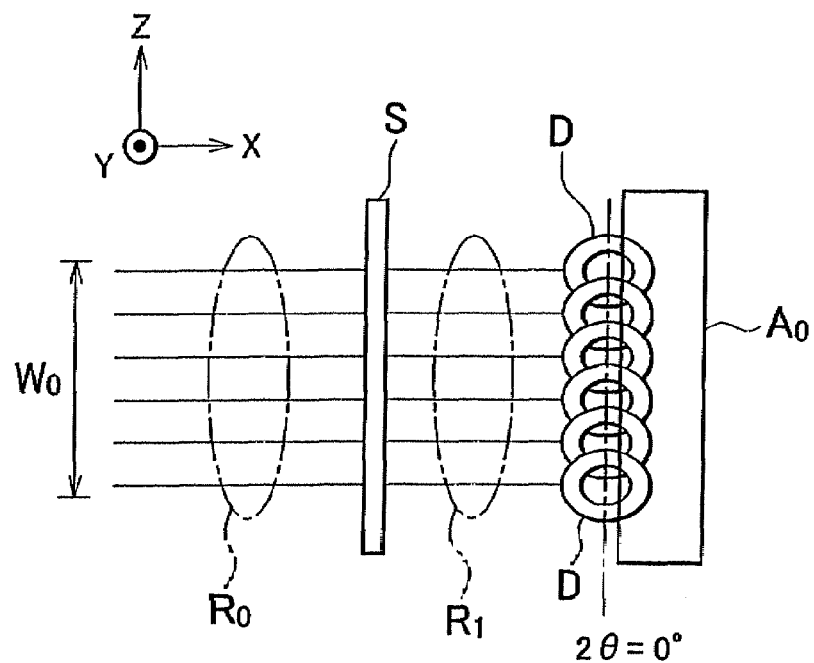
FIGS. 13A and 13B are illustrations of a smearing phenomenon.
Figure 13B:
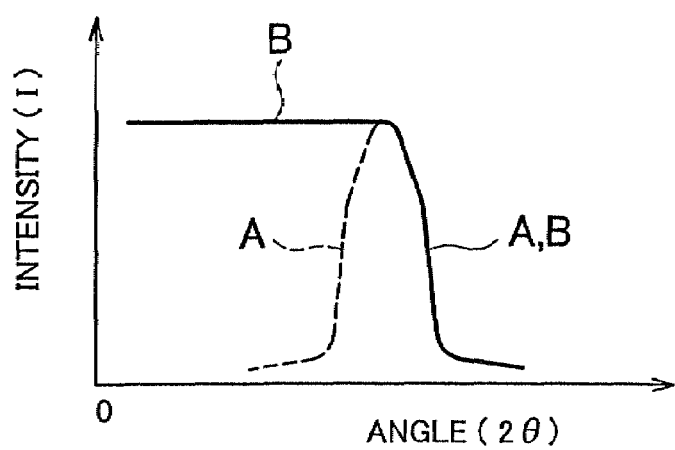

(1) Conventionally, a smearing phenomenon as described above by referring to FIG. 13 appears in the latitudinal direction (Z-direction) because the prior art only controls dispersions in the equatorial plane (XY plane) of X-rays to maintain a degree of parallelism by means of a monochromator 22 and an analyzer 23. Therefore, the accuracy of detection of scattered rays in an ultra-small angle region is poor with the prior art. To the contrary, this embodiment collimates X-rays also in the latitudinal direction (Z-direction) by means of an X-ray collimating mirror 16 so that it is possible to suppress the appearance of a smearing phenomenon in the latitudinal direction. Additionally, since the X-ray collimating mirror 16 is formed by a multilayer film in this embodiment, the X-ray collimating mirror 16 may produce parallel beams having a strong intensity. As a result, it is possible to clearly capture the scattered rays in the ultra-small angle region without being hindered by background components.

(2) When the distance between the sample S and the X-ray detector 7 is 200 mm, the angle of dispersion of X-rays in the latitudinal direction (Z-direction) is about 0.28° with the prior art and 0.06° with this embodiment. In short, in the present embodiment, the angle of dispersion of X-rays in the latitudinal direction is remarkably reduced to by turn remarkably improve the parallelism of X-rays. As a result, it is possible to clearly capture the scattered rays produced in the latitudinal direction.

(3) The intensity of X-rays entering the sample S is about three times stronger with the device of this embodiment than with any device of the prior art that does not comprise an X-ray collimating mirror 16. Then, as a result, it is possible to obtain scattered rays with a sufficient intensity from the sample S to consequently raise the reliability of measurement.

(4) The conventional Bonse-Hart optical system employs line-focused X-rays having a large focus size as X-ray source in order to obtain X-rays with a strong intensity. However, with this technique, it is difficult to achieve a good parallelism and a strong intensity for an X-ray beam in two different directions (in other words in two-dimensional directions). To the contrary, with this embodiment, it is possible to obtain a good parallelism and a strong intensity of X-rays in two-dimensional directions that the conventional Bonse-Hart optical system cannot realize by combining point-focused X-ray of a micro focus, an X-ray collimating mirror formed by using paraboloidal multilayer films, a monochromator formed by using a channel-cut crystal of germanium or silicon and an analyzer also formed by using a channel-cut crystal.

(5) This embodiment can suppress the attenuation of the intensity of X-rays at the monochromator 22 formed by using a channel-cut crystal because X-rays entering the monochromator 22 are highly precisely collimated by means of an X-ray collimating mirror 16.

While the present invention is described above by way of a preferred embodiment, the present invention is by no means limited to the above-described embodiment, which may be modified in various different ways without departing from the scope of the present invention as defined in the appended claims.

For example, any of the X-ray generator 2, the sample support device 24, the analyzer support device 31 and the X-ray detector 7 can be modified for its configuration whenever necessary. Additionally, the four-quadrant slits 34a, 34 may be omitted.

What is claimed is:

1. An ultra-small angle X-ray scattering measuring apparatus comprising:
    an X-ray generation device for emitting X-rays radiated from an X-ray real focus with a predetermined focus size toward a sample;
    an X-ray detection device for detecting X-rays emitted from the sample;
    an X-ray collimating mirror arranged between the X-ray real focus and the sample;
    a monochromator arranged between the X-ray collimating mirror and the sample; and
    an analyzer arranged between the sample and the X-ray detection device, wherein:
    said X-ray collimating mirror includes a first mirror and a second mirror arranged orthogonally relative to each other, the first mirror and the second mirror each having a multilayer film formed by alternately laying layers of a heavy element and layers of a light element so as to operate as an X-ray reflection surface;
    the multilayer film has a profile of a paraboloid, and is comprised of lattice places having an interplanar spacing, the interplanar spacing of the lattice planes of the multilayer film being made to continuously change along the paraboloid so as to satisfy the Bragg's condition for diffraction at any arbitrarily selected position on the X-ray reflection surface relative to X-rays of a specific wavelength;
    the monochromator and the analyzer each have a pair of oppositely disposed X-ray reflection surfaces and are formed of a perfect crystal;
    while the analyzer is driven to rotate for scanning around a 2θ-axial line orthogonal relative to an X-ray optical axis running through the analyzer, the X-ray detection device is configured to detect X-rays at every angular position within the scanning rotation of the analyzer; and
    the first mirror and the second mirror are inclined respectively relative to a plane which includes the X-ray optical axis and is orthogonal to the 2θ-axial line by an angle of 45 degrees.

2. The ultra-small angle X-ray scattering measuring apparatus according to claim 1, wherein
    the X-ray detection device is a zero-dimensional X-ray detector having an aperture for taking in X-rays and is configured to output the intensity of X-rays without spatial resolution on the X-rays taken in through the aperture.

3. The ultra-small angle X-ray scattering measuring apparatus according to claim 2, wherein
    the X-ray generation device takes out point-focused X-rays having a diameter of not smaller than 50 μm and not greater than 100 μm, and a distance between a center of the X-ray real focus and a center of the X-ray collimating mirror is not smaller than 70 mm and not greater than 145 mm.

4. The ultra-small angle X-ray scattering measuring apparatus according to claim 3, wherein
the heavy element is Ni (nickel) and the light element is carbon.

5. The ultra-small angle X-ray scattering measuring apparatus according to claim 4, further comprising:
a four-quadrant slit for controlling the vertical and transversal widths of X-rays entering the monochromator;
a four-quadrant slit for controlling the vertical and transversal widths of X-rays coming out from the monochromator; and
an X-ray absorption member for attenuating the intensity of the direct beam;
wherein the four-quadrant slits and the X-ray absorption member are arranged on the X-ray optical axis.

6. The ultra-small angle X-ray scattering measuring apparatus according to claim 5, further comprising:
a sample support device for supporting the sample, the sample support device having a φ-rotary system for changing an intra-planar angle of the sample around a φ-axial line intersecting an X-ray receiving surface of the sample to detect data by changing angles of lattice planes of the sample relative to incident X-rays.

7. The ultra-small angle X-ray scattering measuring apparatus according to claim 6,
wherein the X-ray detection device is configured to have an angular range of observation thereof adjusted either by translating the analyzer in a direction orthogonal relative to both the X-ray optical axis and the 2θ-axial line, or
by rotating the analyzer around a sample axial line passing through the sample, extending in the direction same as the 2θ-axial line and being orthogonal relative to the X-ray optical axis.

8. An ultra-small angle X-ray scattering measuring apparatus comprising:
an X-ray generation device for emitting X-rays radiated from an X-ray real focus with a predetermined focus size toward a sample;
an X-ray detection device for detecting X-rays emitted from the sample;
an X-ray collimating mirror arranged between the X-ray real focus and the sample;
a monochromator arranged between the X-ray collimating mirror and the sample; and
an analyzer arranged between the sample and the X-ray detection device, wherein:
the analyzer is configured to be driven to rotate for scanning around a 2θ-axial line to detect scattered rays from the sample, the 2θ-axial line being orthogonal relative to an X-ray optical axis extending from the X-ray real focus to the X-ray detection device;
the X-ray collimating mirror is a composite X-ray mirror having two paraboloidal multilayer film X-ray reflection surfaces so as to make the beam of X-rays emitted from the X-ray generation device have a rhombic cross section,
the monochromator and the analyzer are channel-cut crystals for controlling divergence of X-rays in the intra-equatorial-plane containing the X-ray optical axis and perpendicular to the 2θ-axial line;
the X-ray detection device is configured to detect X-rays emitted from the analyzer; and
the composite X-ray mirror is inclined relative to a plane which includes the X-ray optical axis and which is orthogonal to the 2θ-axial line by an angle of 45 degrees.

9. The ultra-small angle X-ray scattering measuring apparatus according to claim 8, further comprising:
a sample support device for supporting the sample, the sample support device having a φ-rotary system for changing an intra-planar angle of the sample around the φ-axial line intersecting an X-ray receiving surface of the sample to detect data by changing angles of lattice planes of the sample relative to incident X-rays.

10. The ultra-small angle X-ray scattering measuring apparatus according to 9, wherein
the X-ray detection device is configured to have an angular range of observation thereof adjusted either by translating the analyzer in a direction orthogonal relative to both the X-ray optical axis and the 2θ-axial line, or
by rotating the analyzer around a sample axial line passing through the sample, extending in the direction same as the 2θ-axial line and being orthogonal relative to the X-ray optical axis.

* * * * *